(12) United States Patent
Lee et al.

(10) Patent No.: US 12,076,069 B2
(45) Date of Patent: Sep. 3, 2024

(54) METHODS AND SYSTEMS FOR LOCATING AND TREATING NERVES WITH COLD THERAPY

(71) Applicant: Pacira CryoTech, Inc., Parsippany, NJ (US)

(72) Inventors: Ann S. Lee, San Francisco, CA (US); Matt Antonelli, Oakland, CA (US); Badier Velji, Mountain View, CA (US); Jessica Preciado Dummett, Dublin, CA (US)

(73) Assignee: Pacira CryoTech, Inc., Tampa, FL (US)

( * ) Notice: Subject to any disclaimer, the term of this patent is extended or adjusted under 35 U.S.C. 154(b) by 103 days.

(21) Appl. No.: 17/700,036

(22) Filed: Mar. 21, 2022

(65) Prior Publication Data

US 2022/0280218 A1    Sep. 8, 2022

Related U.S. Application Data

(63) Continuation of application No. 15/594,238, filed on May 12, 2017, now Pat. No. 11,311,327.
(Continued)

(51) Int. Cl.
*A61B 18/02*    (2006.01)
*A61B 5/00*    (2006.01)
(Continued)

(52) U.S. Cl.
CPC ............ *A61B 18/0218* (2013.01); *A61B 5/05* (2013.01); *A61B 5/4893* (2013.01); *A61B 18/02* (2013.01);
(Continued)

(58) Field of Classification Search
CPC ................ A61B 18/02; A61B 18/0218; A61B 2018/0262; A61B 2018/0293; A61B 5/4893
See application file for complete search history.

(56) References Cited

U.S. PATENT DOCUMENTS 2,319,542 A    5/1943  Hall
2,672,032 A    3/1964  Towse
(Continued)

FOREIGN PATENT DOCUMENTS

CA    2643474    9/2007
DE    1402632    8/1975
(Continued)

OTHER PUBLICATIONS

"Cryoablation in Pain Management", Brochure, Metrum CryoFlex, Medical Devices Manufacturer, 2012, 5 pages.
(Continued)

*Primary Examiner* — Tigist S Demie
(74) *Attorney, Agent, or Firm* — Kilpatrick Townsend & Stockton LLP

(57) ABSTRACT

The present invention generally relates to improved medical devices, systems, and methods. In many embodiments, devices, systems, and methods for locating and treating a target nerve with cold therapy are provided. For example, a focused cold therapy treatment device may be provided that is adapted to couple with or be fully integrated with a nerve stimulation device such that nerve stimulation and focused cold therapy may be performed concurrently with the cryo-stimulation device. Improvements in nerve localization and targeting may increase treatment accuracy and physician confidence in needle placement during treatment. In turn, such improvements may decrease overall treatment times, the number of repeat treatments, and the re-treatment rate. Further, additional improvements in nerve localization and (Continued)

targeting may reduce the number of applied treatment cycles and may also reduce the number of cartridge changes (when replaceable refrigerant cartridges are used).

18 Claims, 23 Drawing Sheets

Related U.S. Application Data

(60) Provisional application No. 62/336,241, filed on May 13, 2016.

(51) Int. Cl.
  *A61B 5/05* (2021.01)
  *A61B 18/00* (2006.01)

(52) U.S. Cl.
  CPC .. *A61B 18/0206* (2013.01); *A61B 2018/0022* (2013.01); *A61B 2018/00226* (2013.01); *A61B 2018/00434* (2013.01); *A61B 2018/00583* (2013.01); *A61B 2018/0262* (2013.01); *A61B 2018/0293* (2013.01)

(56) References Cited

U.S. PATENT DOCUMENTS

| | | |
|---|---|---|
| 3,226,492 A | 12/1965 | Schuetze |
| 3,266,492 A | 8/1966 | Steinberg |
| 3,289,424 A | 12/1966 | Shepherd |
| 3,343,544 A | 9/1967 | Dunn et al. |
| 3,351,063 A | 11/1967 | Malaker et al. |
| 3,439,680 A | 4/1969 | Thomas, Jr. |
| 3,483,869 A | 12/1969 | Hayhurst |
| 3,502,081 A | 3/1970 | Amoils |
| 3,507,283 A | 4/1970 | Thomas, Jr. |
| 3,532,094 A | 10/1970 | Stahl |
| 3,664,344 A | 5/1972 | Bryne |
| 3,702,114 A | 11/1972 | Zacarian |
| 3,795,245 A | 3/1974 | Allen, Jr. et al. |
| 3,814,095 A | 6/1974 | Lubens |
| 3,830,239 A | 8/1974 | Stumpf et al. |
| 3,886,945 A | 6/1975 | Stumpf et al. |
| 3,889,681 A | 6/1975 | Waller et al. |
| 3,951,152 A | 4/1976 | Crandell et al. |
| 3,993,075 A | 11/1976 | Lisenbee et al. |
| 4,140,109 A | 2/1979 | Savic et al. |
| 4,207,897 A | 6/1980 | Lloyd et al. |
| 4,236,518 A | 12/1980 | Floyd |
| 4,306,568 A | 12/1981 | Torre |
| 4,376,376 A | 3/1983 | Gregory |
| 4,404,862 A | 9/1983 | Harris, Sr. |
| 4,524,771 A | 6/1985 | McGregor et al. |
| 4,758,217 A | 7/1988 | Gueret |
| 4,946,460 A | 8/1990 | Merry et al. |
| 5,059,197 A | 10/1991 | Urie et al. |
| 5,200,170 A | 4/1993 | McDow |
| 5,294,325 A | 3/1994 | Liu |
| 5,334,181 A | 8/1994 | Rubinsky et al. |
| 5,520,681 A | 5/1996 | Fuller et al. |
| 5,571,147 A | 11/1996 | Sluijter et al. |
| 5,647,868 A | 7/1997 | Chinn |
| 5,747,777 A | 5/1998 | Matsuoka |
| 5,755,753 A | 5/1998 | Knowlton |
| 5,814,040 A | 9/1998 | Nelson et al. |
| 5,860,970 A | 1/1999 | Goddard et al. |
| 5,879,378 A | 3/1999 | Usui |
| 5,899,897 A | 5/1999 | Rabin et al. |
| 5,916,212 A | 6/1999 | Baust et al. |
| 5,976,505 A | 11/1999 | Henderson |
| 6,003,539 A | 12/1999 | Yoshihara |
| 6,032,675 A | 3/2000 | Rubinsky |
| 6,039,730 A | 3/2000 | Rabin et al. |
| 6,041,787 A | 3/2000 | Rubinsky |
| 6,139,545 A | 10/2000 | Utley et al. |
| 6,141,985 A | 11/2000 | Cluzeau et al. |
| 6,142,991 A | 11/2000 | Schatzberger |
| 6,182,666 B1 | 2/2001 | Dobak, III |
| 6,196,839 B1 | 3/2001 | Ross |
| 6,238,386 B1 | 5/2001 | Muller et al. |
| 6,277,099 B1 | 8/2001 | Strowe et al. |
| 6,277,116 B1 | 8/2001 | Utely et al. |
| 6,312,392 B1 | 11/2001 | Herzon |
| 6,363,730 B1 | 4/2002 | Thomas et al. |
| 6,364,899 B1 | 4/2002 | Dobak, III |
| 6,371,943 B1 | 4/2002 | Racz et al. |
| 6,379,348 B1 | 4/2002 | Onik |
| 6,432,102 B2 | 8/2002 | Joye et al. |
| 6,494,844 B1 | 12/2002 | Van Bladel et al. |
| 6,503,246 B1 | 1/2003 | Har-Shai et al. |
| 6,506,796 B1 | 1/2003 | Fesus et al. |
| 6,546,935 B2 | 4/2003 | Hooven |
| 6,551,309 B1 | 4/2003 | LePivert |
| 6,562,030 B1 | 5/2003 | Abboud et al. |
| 6,629,951 B2 | 10/2003 | Laufer et al. |
| 6,648,880 B2 | 11/2003 | Chauvet et al. |
| 6,669,688 B2 | 12/2003 | Svaasand et al. |
| 6,672,095 B1 | 1/2004 | Luo |
| 6,682,501 B1 | 1/2004 | Nelson et al. |
| 6,706,037 B2 | 3/2004 | Zvuloni et al. |
| 6,723,092 B2 | 4/2004 | Brown et al. |
| 6,749,624 B2 | 6/2004 | Knowlton |
| 6,761,715 B2 | 7/2004 | Carroll |
| 6,764,493 B1 | 7/2004 | Weber et al. |
| 6,786,901 B2 | 9/2004 | Joye et al. |
| 6,786,902 B1 | 9/2004 | Rabin et al. |
| 6,789,545 B2 | 9/2004 | Littrup et al. |
| 6,840,935 B2 | 1/2005 | Lee |
| 6,858,025 B2 | 2/2005 | Maurice |
| 6,896,666 B2 | 5/2005 | Kochamba |
| 6,902,554 B2 | 6/2005 | Huttner |
| 6,905,492 B2 | 6/2005 | Zvuloni et al. |
| 6,905,494 B2 | 6/2005 | Yon et al. |
| 6,936,048 B2 | 8/2005 | Hurst |
| 6,960,208 B2 | 11/2005 | Bourne et al. |
| 7,001,400 B1 | 2/2006 | Modesitt et al. |
| 7,081,111 B2 | 7/2006 | Svaasand et al. |
| 7,081,112 B2 | 7/2006 | Joye et al. |
| 7,083,612 B2 | 8/2006 | Littrup et al. |
| 7,189,230 B2 | 3/2007 | Knowlton |
| 7,195,616 B2 | 3/2007 | Diller et al. |
| 7,207,985 B2 | 4/2007 | Duong et al. |
| 7,217,939 B2 | 5/2007 | Johansson et al. |
| 7,250,046 B1 | 7/2007 | Fallat |
| 7,278,991 B2 | 10/2007 | Morris et al. |
| 7,311,672 B2 | 12/2007 | Van Bladel et al. |
| 7,322,973 B2 | 1/2008 | Nahon |
| 7,338,504 B2 | 3/2008 | Gibbens et al. |
| 7,347,840 B2 | 3/2008 | Findlay et al. |
| 7,367,341 B2 | 5/2008 | Anderson et al. |
| 7,402,140 B2 | 7/2008 | Spero et al. |
| 7,422,586 B2 | 9/2008 | Morris et al. |
| 7,479,139 B2 | 1/2009 | Cytron et al. |
| 7,549,424 B2 | 6/2009 | Desai |
| 7,578,819 B2 | 8/2009 | Bleich et al. |
| 7,620,290 B2 | 11/2009 | Rizoiu et al. |
| 7,641,679 B2 | 1/2010 | Joye et al. |
| 7,653,438 B2 | 1/2010 | Deem et al. |
| 7,713,266 B2 | 5/2010 | Elkins et al. |
| 7,842,047 B2 | 11/2010 | Modesitt et al. |
| 7,846,170 B2 | 12/2010 | Modesitt et al. |
| 7,850,683 B2 | 12/2010 | Elkins et al. |
| 7,862,558 B2 | 1/2011 | Elkins et al. |
| 7,998,137 B2 | 8/2011 | Elkins et al. |
| 8,027,718 B2 | 9/2011 | Spinner et al. |
| 8,038,688 B2 | 10/2011 | Modesitt et al. |
| 8,298,216 B2 | 10/2012 | Burger et al. |
| 8,409,185 B2 | 4/2013 | Burger et al. |
| 8,461,108 B2 | 6/2013 | Hsu et al. |
| 8,617,228 B2 | 12/2013 | Wittenberger et al. |
| 8,715,275 B2 | 5/2014 | Burger et al. |
| 8,722,065 B2 | 5/2014 | Ishibashi et al. |
| 9,017,318 B2 | 4/2015 | Fourkas et al. |
| 9,039,688 B2 | 5/2015 | Palmer, III et al. |

(56) References Cited

U.S. PATENT DOCUMENTS

| | | |
|---|---|---|
| 9,066,712 B2 | 6/2015 | Fourkas et al. |
| 9,101,346 B2 | 8/2015 | Burger et al. |
| 9,113,912 B1 | 8/2015 | Mehta et al. |
| 9,155,584 B2 | 10/2015 | Fourkas et al. |
| 9,241,753 B2 | 1/2016 | Fourkas et al. |
| 9,254,162 B2 | 2/2016 | Burger et al. |
| 9,295,512 B2 | 3/2016 | Allison et al. |
| 9,314,290 B2 | 4/2016 | Fourkas et al. |
| 9,585,618 B2 | 3/2017 | Leschinsky et al. |
| 10,130,409 B2 | 11/2018 | Hinton et al. |
| 10,888,366 B2 | 1/2021 | Allison |
| 2002/0010460 A1 | 1/2002 | Joye et al. |
| 2002/0013602 A1 | 1/2002 | Huttner |
| 2002/0045434 A1 | 4/2002 | Masoian et al. |
| 2002/0049436 A1 | 4/2002 | Zvuloni et al. |
| 2002/0068929 A1 | 6/2002 | Zvuloni |
| 2002/0120260 A1 | 8/2002 | Morris et al. |
| 2002/0120261 A1 | 8/2002 | Morris et al. |
| 2002/0120263 A1 | 8/2002 | Brown et al. |
| 2002/0128638 A1 | 9/2002 | Chauvet et al. |
| 2002/0156469 A1 | 10/2002 | Yon et al. |
| 2002/0183731 A1 | 12/2002 | Holland et al. |
| 2002/0193778 A1 | 12/2002 | Alchas et al. |
| 2003/0036752 A1 | 2/2003 | Joye et al. |
| 2003/0109912 A1 | 6/2003 | Joye et al. |
| 2003/0130575 A1 | 7/2003 | Desai |
| 2003/0144709 A1 | 7/2003 | Zabara et al. |
| 2003/0181896 A1 | 9/2003 | Zvuloni et al. |
| 2003/0195436 A1 | 10/2003 | Van Bladel et al. |
| 2003/0220635 A1 | 11/2003 | Knowlton et al. |
| 2003/0220674 A1 | 11/2003 | Anderson et al. |
| 2004/0024391 A1 | 2/2004 | Cytron et al. |
| 2004/0082943 A1 | 4/2004 | Littrup et al. |
| 2004/0092875 A1 | 5/2004 | Kochamba |
| 2004/0122482 A1 | 6/2004 | Tung et al. |
| 2004/0143252 A1 | 7/2004 | Hurst |
| 2004/0162551 A1 | 8/2004 | Brown et al. |
| 2004/0167505 A1 | 8/2004 | Joye et al. |
| 2004/0191229 A1 | 9/2004 | Link, Jr. et al. |
| 2004/0204705 A1 | 10/2004 | Lafontaine |
| 2004/0210212 A1 | 10/2004 | Maurice |
| 2004/0215178 A1 | 10/2004 | Maurice |
| 2004/0215294 A1 | 10/2004 | Littrup et al. |
| 2004/0215295 A1 | 10/2004 | Littrup et al. |
| 2004/0220497 A1 | 11/2004 | Findlay et al. |
| 2004/0220648 A1 | 11/2004 | Carroll |
| 2004/0225276 A1 | 11/2004 | Burgess |
| 2004/0243116 A1 | 12/2004 | Joye et al. |
| 2004/0267248 A1 | 12/2004 | Duong et al. |
| 2004/0267257 A1 | 12/2004 | Bourne et al. |
| 2005/0004563 A1 | 1/2005 | Racz et al. |
| 2005/0177147 A1 | 8/2005 | Vancelette et al. |
| 2005/0177148 A1 | 8/2005 | van der Walt et al. |
| 2005/0182394 A1 | 8/2005 | Spero et al. |
| 2005/0203505 A1 | 9/2005 | Megerman et al. |
| 2005/0203593 A1 | 9/2005 | Shanks et al. |
| 2005/0209565 A1 | 9/2005 | Yuzhakov et al. |
| 2005/0209587 A1 | 9/2005 | Joye et al. |
| 2005/0224086 A1 | 10/2005 | Nahon |
| 2005/0228288 A1 | 10/2005 | Hurst |
| 2005/0251103 A1 | 11/2005 | Steffen et al. |
| 2005/0261753 A1 | 11/2005 | Littrup et al. |
| 2005/0276759 A1 | 12/2005 | Roser et al. |
| 2005/0281530 A1 | 12/2005 | Rizoiu et al. |
| 2005/0283148 A1 | 12/2005 | Janssen et al. |
| 2006/0009712 A1 | 1/2006 | Van Bladel et al. |
| 2006/0015092 A1 | 1/2006 | Joye et al. |
| 2006/0069385 A1 | 3/2006 | Lafontaine et al. |
| 2006/0079914 A1 | 4/2006 | Modesitt et al. |
| 2006/0084962 A1 | 4/2006 | Joye et al. |
| 2006/0089688 A1 | 4/2006 | Panescu |
| 2006/0111732 A1 | 5/2006 | Gibbens et al. |
| 2006/0129142 A1 | 6/2006 | Reynolds |
| 2006/0142785 A1 | 6/2006 | Modesitt et al. |
| 2006/0173469 A1 | 8/2006 | Klein et al. |
| 2006/0189968 A1 | 8/2006 | Howlett et al. |
| 2006/0190035 A1 | 8/2006 | Hushka et al. |
| 2006/0200117 A1 | 9/2006 | Hermans |
| 2006/0212028 A1 | 9/2006 | Joye et al. |
| 2006/0212048 A1 | 9/2006 | Crainich |
| 2006/0223052 A1 | 10/2006 | MacDonald et al. |
| 2006/0224149 A1 | 10/2006 | Hillely |
| 2006/0241648 A1 | 10/2006 | Bleich et al. |
| 2006/0258951 A1 | 11/2006 | Bleich et al. |
| 2007/0060921 A1 | 3/2007 | Janssen et al. |
| 2007/0088217 A1 | 4/2007 | Babaev |
| 2007/0129714 A1 | 6/2007 | Elkins et al. |
| 2007/0156125 A1 | 7/2007 | DeLonzor |
| 2007/0161975 A1 | 7/2007 | Goulko |
| 2007/0167943 A1 | 7/2007 | Janssen et al. |
| 2007/0167959 A1 | 7/2007 | Modesitt et al. |
| 2007/0179509 A1 | 8/2007 | Nagata et al. |
| 2007/0198071 A1 | 8/2007 | Ting et al. |
| 2007/0225781 A1 | 9/2007 | Saadat et al. |
| 2007/0255362 A1 | 11/2007 | Levinson et al. |
| 2007/0270925 A1 | 11/2007 | Levinson |
| 2008/0051775 A1 | 2/2008 | Evans |
| 2008/0051776 A1 | 2/2008 | Bliweis et al. |
| 2008/0077201 A1 | 3/2008 | Levinson et al. |
| 2008/0077202 A1 | 3/2008 | Levinson |
| 2008/0077211 A1 | 3/2008 | Levinson et al. |
| 2008/0154254 A1 | 6/2008 | Burger et al. |
| 2008/0183164 A1 | 7/2008 | Elkins et al. |
| 2008/0200910 A1 | 8/2008 | Burger et al. |
| 2008/0228250 A1 | 9/2008 | Mironer |
| 2008/0287839 A1 | 11/2008 | Rosen et al. |
| 2009/0018623 A1 | 1/2009 | Levinson et al. |
| 2009/0018624 A1 | 1/2009 | Levinson et al. |
| 2009/0018625 A1 | 1/2009 | Levinson et al. |
| 2009/0018626 A1 | 1/2009 | Levinson et al. |
| 2009/0018627 A1 | 1/2009 | Levinson et al. |
| 2009/0118722 A1 | 5/2009 | Ebbers et al. |
| 2009/0171334 A1 | 7/2009 | Elkins et al. |
| 2009/0248001 A1 | 10/2009 | Burger et al. |
| 2009/0264876 A1 | 10/2009 | Roy et al. |
| 2009/0299357 A1 | 12/2009 | Zhou |
| 2010/0114191 A1 | 5/2010 | Newman |
| 2010/0168725 A1 | 7/2010 | Babkin et al. |
| 2010/0274237 A1 | 10/2010 | Yamakawa et al. |
| 2010/0305439 A1 | 12/2010 | Shai et al. |
| 2010/0331883 A1 | 12/2010 | Schmitz et al. |
| 2011/0144631 A1 | 6/2011 | Elkins et al. |
| 2011/0178514 A1 | 7/2011 | Levin et al. |
| 2011/0196267 A1 | 8/2011 | Mishelevich |
| 2012/0065629 A1 | 3/2012 | Elkins et al. |
| 2012/0089211 A1 | 4/2012 | Curtis et al. |
| 2012/0259322 A1 | 10/2012 | Fourkas et al. |
| 2012/0265187 A1 | 10/2012 | Palmer, III et al. |
| 2013/0218148 A1 | 8/2013 | Burger et al. |
| 2013/0253605 A1 | 9/2013 | Bennett et al. |
| 2013/0324990 A1 | 12/2013 | Burger et al. |
| 2014/0249519 A1* | 9/2014 | Burger .................. A61F 7/12 606/20 |
| 2014/0276539 A1 | 9/2014 | Allison et al. |
| 2014/0276708 A1 | 9/2014 | Karnik et al. |
| 2014/0343542 A1 | 11/2014 | Karnik et al. |
| 2014/0343543 A1* | 11/2014 | Karnik .................. A61B 18/02 606/24 |
| 2014/0343544 A1 | 11/2014 | Carnell et al. |
| 2015/0011930 A1 | 1/2015 | Yamanishi et al. |
| 2015/0112405 A1 | 4/2015 | Brown et al. |
| 2016/0000601 A1 | 1/2016 | Burger et al. |
| 2016/0166429 A1 | 6/2016 | Allison et al. |

FOREIGN PATENT DOCUMENTS

| | | |
|---|---|---|
| EP | 0043447 | 1/1982 |
| EP | 0955012 A1 | 11/1999 |
| EP | 1074273 | 2/2001 |
| EP | 1377327 B1 | 9/2007 |
| EP | 1862125 | 12/2007 |
| EP | 2499984 A1 | 9/2012 |
| GB | 1402632 | 8/1975 |
| JP | 10014656 A | 1/1998 |

(56) References Cited

FOREIGN PATENT DOCUMENTS

| | | |
|---|---|---|
| JP | 2001178737 A | 7/2001 |
| JP | 2005080988 A | 3/2005 |
| JP | 2006130055 A | 5/2006 |
| JP | 2008515469 A | 5/2008 |
| RU | 2254060 C2 | 6/2005 |
| WO | 9749344 A1 | 12/1997 |
| WO | 0197702 A1 | 12/2001 |
| WO | 0202026 A1 | 1/2002 |
| WO | 02092153 A2 | 11/2002 |
| WO | 2004039440 | 5/2004 |
| WO | 2004045434 A2 | 6/2004 |
| WO | 2004089460 | 10/2004 |
| WO | 2005000106 | 1/2005 |
| WO | 2005079321 | 9/2005 |
| WO | 2005096979 A1 | 10/2005 |
| WO | 2006012128 | 2/2006 |
| WO | 2006023348 A1 | 3/2006 |
| WO | 2006044727 A2 | 4/2006 |
| WO | 2006062788 A2 | 6/2006 |
| WO | 2006125835 A1 | 11/2006 |
| WO | 2006127467 A2 | 11/2006 |
| WO | 2007025106 A2 | 3/2007 |
| WO | 2007037326 A1 | 4/2007 |
| WO | 2007089603 | 8/2007 |
| WO | 2007109656 A2 | 9/2007 |
| WO | 2007129121 | 11/2007 |
| WO | 2007135629 | 11/2007 |
| WO | 2009026471 | 2/2009 |
| WO | 2010075438 A1 | 7/2010 |
| WO | 2010075448 A1 | 7/2010 |
| WO | 2014146105 A2 | 9/2014 |
| WO | 2014146106 A2 | 9/2014 |
| WO | 2014146122 A1 | 9/2014 |
| WO | 2014146127 A1 | 9/2014 |

OTHER PUBLICATIONS

"Cryoprobe", One Med Group, LLC, Available online at: http://www.onemedgroup.com/, Feb. 4, 2008, pp. 1-2.

"Cryosurgery Probes and Accessories Catalogue", Metrum CryoFlex, Contact Probes Catalogue, 2009, 25 pages.

"CyroPen, LLC Launches Revolutionary, State-of-the-Art Medical Device the Future of Cryosurgery in a Pen", Press Release, Available online at: http://cryopen.com/press.htm, Apr. 27, 2006, pp. 1-3.

"New Technology Targets Motor Nerves", Advanced Cosmetic Intervention, Inc., Available Online at: http://www.acisurgery.com, 2007, 1 page.

"The CryoProbe™—Excellence in Cryosurgery", Cryosurgical Concepts, Inc., Available online at: http://www.cryo-surgical.com, Feb. 8, 2008, pp. 1-2.

"The Future of Cryosurgery at Your Fingertips", CryoPen, LLC, Available online at: http://cryopen.com/, 2006-2008, 2 pages.

U.S. Appl. No. 61/116,050, Cryosurgical Safety Valve Arrangement and Methods for Its Use in Cosmetic and Other Treatment, Nov. 19, 2008, 35 pages.

Bohannon et al., "Interrater Reliability of a Modified Ashworth Scale of Muscle Spasticity", Phys Ther., vol. 67, No. 2, Feb. 1987, pp. 206-207.

Boyd et al., "Objective Measurement of Clinical Findings in the Use of Botulinum Toxin Type A for the Management of Children with Cerebral Palsy", European Journal of Neurology, vol. 6, Supp. S4, 1999, pp. S23-S35.

Dasiou-Plakida, "Fat Injections for Facial Rejuvenation: 17 Years Experience in 1720 Patients", Journal of Cosmetic Dermatology, vol. 2, Issue 3-4, Oct. 22, 2004, pp. 119-125.

Farrar et al., "Validity, Reliability, and Clinical Importance of Change in a 0-10 Numeric Rating Scale Measure of Spasticity: a Post HOC Analysis of a Randomized, Double-Blind, Placebo-Controlled Trial", Clin Ther., vol. 30, No. 5, 2008, pp. 974-985.

Foster et al., "Radiofrequency Ablation of Facial Nerve Branches Controlling Glabellar Frowning", Dermatol Surg, vol. 35, Issue 12, Dec. 2009, pp. 1908-1917.

Gallagher et al., "Prospective Validation of Clinically Important Changes in Pain Severity Measured on a Visual Analog Scale", Annals of Emergency Medicine, vol. 38, No. 6, 2001, pp. 633-638.

Har-Shai et al., "Effect of Skin Surface Temperature on Skin Pigmentation During Contact and Intralesional Cryosurgery of Hypertrophic Scars and Kleoids", Journal of the European Academy of Dermatology and Venereology, vol. 21, No. 2, Feb. 2007, pp. 1-14.

Magalov et al., "Isothermal Volume Contours Generated in a Freezing Gel by Embedded Cryo-Needles with Applications to Cryo-Surgery", Cryobiology, vol. 55, Issue 2, Oct. 2007, pp. 127-137.

Morris, "Ashworth And Tardieu Scales: Their Clinical Relevance for Measuring Spasticity in Adult And Paediatric Neurological Populations", Physical Therapy Reviews, vol. 7, No. 1, 2002, pp. 53-62.

Page et al., "Clinically Important Differences for the Upper-Extremity Fugl-Meyer Scale in People with Minimal to Moderate Impairment Due to Chronic Stroke", Physical Therapy, vol. 92, No. 6, Jan. 26, 2012, pp. 791-798.

Penn et al., "Intrathecal Baclofen for Severe Spinal Spasticity", N Engl J Med., vol. 320, No. 23, Jun. 8, 1989, pp. 1517-1521.

Rewcastle et al., "A Model for the Time Dependent Three-Dimensional Thermal Distribution within Iceballs Surrounding Multiple Cryoprobes", Medical Physics, vol. 28, Issue 6, Jun. 2001, pp. 1125-1137.

Rutkove, "Effects of Temperature on Neuromuscular Electrophysiology", Muscles and Nerves, vol. 24, Issue 7, Jul. 2001, pp. 867-882.

Shaw et al., "BoTULS: A Multicentre Randomised Controlled Trial to Evaluate the Clinical Effectiveness and Cost-Effectiveness of Treating Upper Limb Spasticity Due to Stroke with Botulinum Toxin Type A", Health Technol Assess., vol. 14, No. 26, May 2010, 158 pages.

Sullivan et al., "Fugl-Meyer Assessment of Sensorimotor Function After Stroke: Standardized Training Procedure for Clinical Practice and Clinical Trials", Stroke, vol. 42, No. 2, Feb. 2011, pp. 427-432.

Utley et al., "Radiofrequency Ablation of the Nerve to the Corrugator Muscle for Elimination of Glabellar Furrowing", Archives of Facial Plastic Surgery, vol. 1, Issue 1, Jan.-Mar. 1999, pp. 46-48.

Yang et al., "Apoptosis Induced by Cryo-Injury in Human Colorectal Cancer Cells is Associated with Mitochondrial Dysfunction", International Journal of Cancer, vol. 103, Issue 3, Jan. 2003, pp. 360-369.

\* cited by examiner

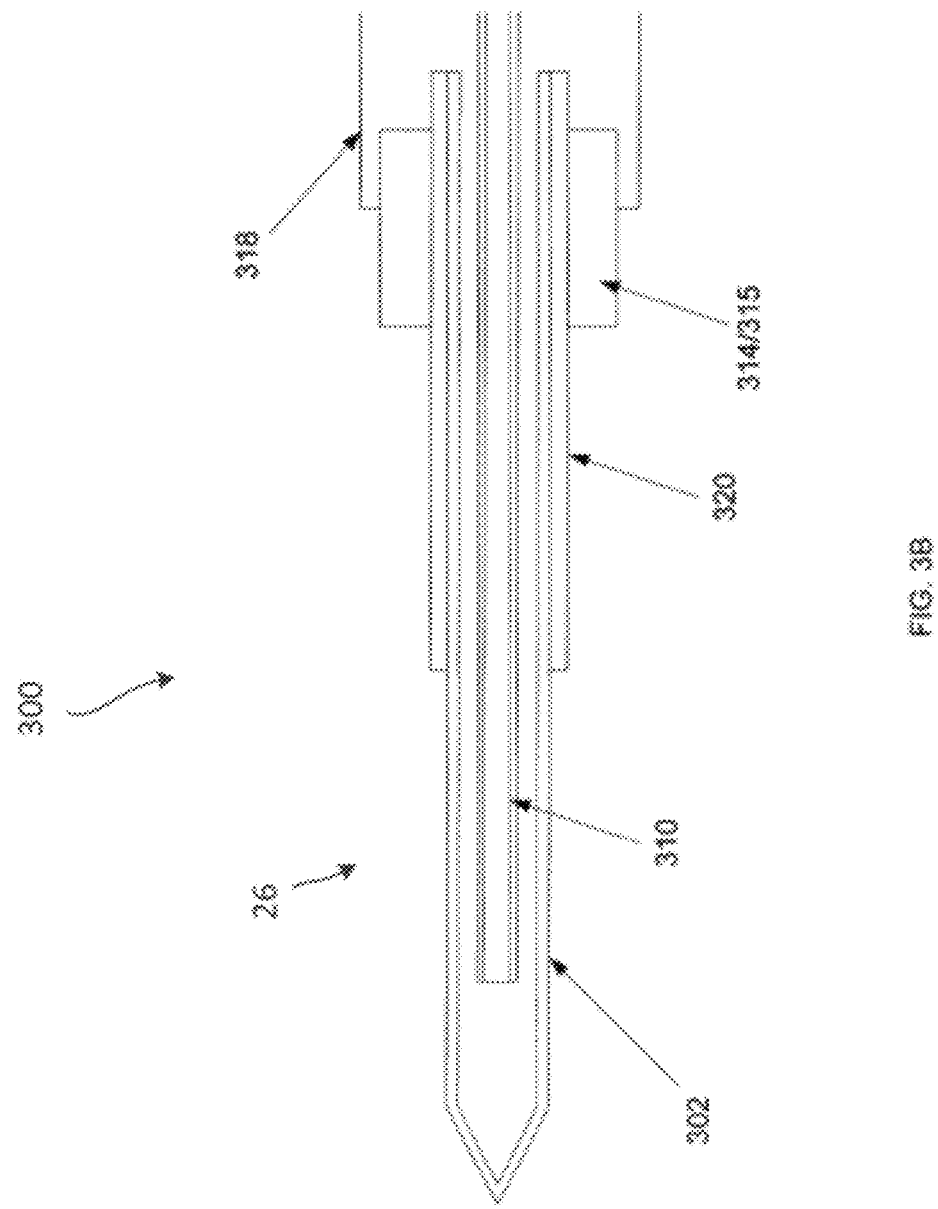

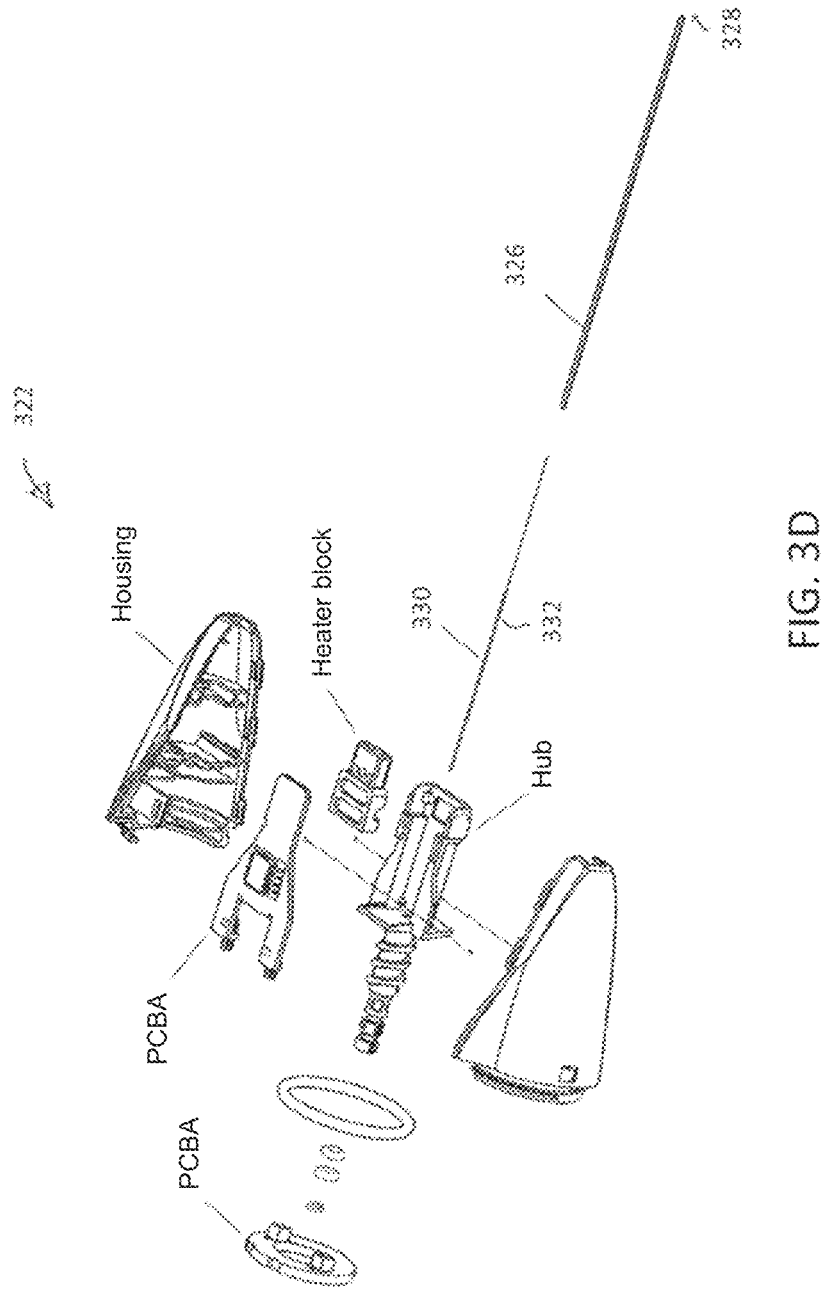

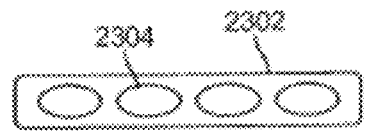
FIG. 8
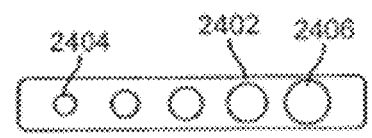
FIG. 9
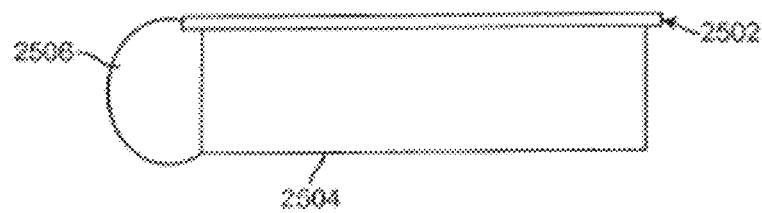
FIG. 10
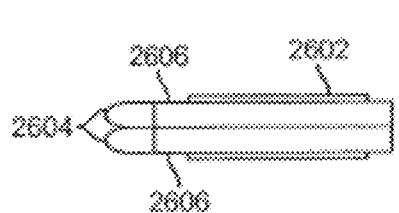 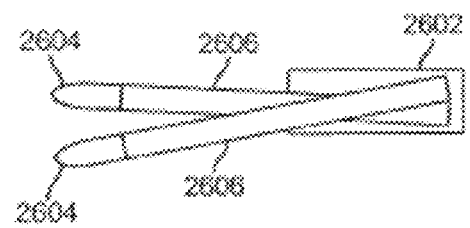
FIG. 11            FIG. 12

METHODS AND SYSTEMS FOR LOCATING AND TREATING NERVES WITH COLD THERAPY

CROSS REFERENCE TO RELATED APPLICATIONS

The present application is a Continuation of U.S. patent application Ser. No. 15/594,238 filed May 12, 2017 (Allowed); which claims the benefit of U.S. Provisional Patent Appln No. 62/336,241 filed May 13, 2016, the full disclosures which are incorporated herein by reference in their entirety for all purposes.

BACKGROUND

The present invention generally relates to improved medical devices, systems, and methods. In many embodiments, devices, systems, and methods for locating and treating a nerve with cold therapy are provided.

Focused Cold Therapy ("FCT") may be used to treat nerves, also referred to as cryoneurolysis or cryoneuroablation, to temporarily stop nerve signaling, typically for a set period of time and may be followed by a restoration of nerve function. FCT can be used on motor nerves for various cosmetic applications and/or medical conditions, including but not limited to: movement disorders, muscle spasms, muscle hyperactivity and/or any condition where reduction in muscle movement is desired. Additionally, FCT may be used on sensory nerves to provide temporary or permanent pain relief by degenerating the nerve and providing a peripheral nerve block. While FCT has many beneficial applications, further improvements in the methods, devices, and systems may be had.

SUMMARY OF THE DISCLOSURE

The present invention generally relates to improved medical devices, systems, and methods. In many embodiments, devices, systems, and methods for locating and treating a target nerve with cold therapy are provided. For example, embodiments of the present disclosure may improve nerve targeting during FCT procedures. Improvements in nerve localization and targeting may increase treatment accuracy and physician confidence in needle placement during treatment. In turn, such improvements may decrease overall treatment times, the number of repeat treatments, and the re-treatment rate. Further, additional improvements in nerve localization and targeting may reduce the number of applied treatment cycles and may also reduce the number of cartridge changes (when replaceable refrigerant cartridges are used). Accordingly, embodiments of the present disclosure may provide one or more advantages for FCT by improving localization and treatment of target nerves.

In some aspects of the present invention, a cryo-stimulation treatment device may be provided. The device may have a needle having a proximal end and a distal end and a length therebetween. The needle may be configured to produce a cold zone for focused cold therapy. The needle may have a cooling center along the length of the needle that is associated with a center of the cold zone produced by the needle. The device may further include an electrically insulative coating disposed about the length of the needle. The needle may be electrically conductive and the proximal end of the needle may be configured to couple with an electrical nerve stimulation generator that generates an electrical field about the distal end of the needle for electrically stimulating and locating the target nerve. The cooling center of the needle may be uninsulated such that an intensity of the electrical field may be co-incident with the center of the cold zone produced by the needle.

In some embodiments, the electrical nerve stimulation generator or waveform generator may be coupled with an uninsulated portion of the proximal end of the needle. A handle may be provided that is defined by a housing. The housing may house the electrical nerve stimulation generator in certain embodiments.

Optionally, a handle may be provided that is defined by a housing. The housing may include an electrical port that electrically couples with an uninsulated portion of the proximal end of the needle. The electrical port may be configured to receive an input associated with the electrical nerve stimulation generator to electrically couple the electrical nerve stimulation generator and the needle.

In some embodiments, the needle may be part of a replaceable needle assembly configured for releasable attachment to a handpiece. The replaceable needle assembly may include an electrical port that electrically couples with an uninsulated portion of the proximal end of the needle. The electrical port may be configured to receive an input associated with the electrical nerve stimulation generator to electrically couple the electrical nerve stimulation generator and the needle.

In some embodiments, the electrically insulated coating comprises a fluoropolymer coating. Optionally, the electrically insulated coating may be a silicone rubber coating, a parylene coating, a ceramic coating, an epoxy coating, or a polyimide coating.

Optionally, the needle may be a first needle of a needle assembly having the first needle and a second needle adjacent the first needle. The second needle may act as an electrical ground during electrical stimulation of the nerve by the first needle.

In further aspects of the present invention, a cryo-stimulation treatment device may be provided that includes a needle assembly having one or more treatment needles configured to produce a cold zone for focused cold therapy of a target nerve. The needle assembly may further include one or more stimulation needles constructed of electrically conductive material and being configured to couple with an electrical nerve stimulation generator to produce an electrical field for stimulating the target nerve. In some embodiments, an electrically insulating coating may be provided on the one or more stimulation needles. The one or more stimulation needles may be uninsulated by the electrically insulating coating at a location of the one or more stimulation needles that is coincident with a center of the cold zone produced by the one or more treatment needles.

The one or more stimulation needles may include a center needle. The one or more treatment needles may include at least two needles that are adjacent the center needle and on opposite sides of the center needle.

Optionally, the one or more treatment needles may include an electrically insulating coating. At least a distal portion of the one or more treatment needles may be uninsulated and may act as an electrical ground during electrical stimulation of the target nerve by the one or more stimulation needles, in certain embodiments.

The one or more treatment needles may also be stimulation needles constructed of electrically conductive material and may be configured to couple with an electrical nerve stimulation generator to produce an electrical field for stimulating the target nerve.

In some embodiments, the device may include a handle defined by a housing. A distal end of the housing may include an electrical adapter that electrically couples the needle assembly to the handle. The housing may house the electrical nerve stimulation generator and connection of the needle assembly to the adapter may electrically couple the one or more stimulation needles with the electrical nerve stimulation generator.

In certain embodiments, a handle may be provided that is defined by a housing. The housing may incorporate an electrical port that electrically couples with an uninsulated portion of the one or more stimulation needles. The electrical port may be configured to receive an input associated with the electrical nerve stimulation generator to electrically couple the electrical nerve stimulation generator and the one or more stimulation needles.

In some embodiments, the needle assembly may be configured for releasable attachment to a handpiece. The replaceable needle assembly may include an electrical port that electrically couples with an uninsulated portion of the one or more stimulating needles. The electrical port may be configured to receive an input associated with the electrical nerve stimulation generator to electrically couple the electrical nerve stimulation generator and the needle.

In still further embodiments, a method of treating a nerve may be provided. The method may include inserting one or more needles of a needle assembly into a tissue of a patient. Thereafter, the nerve may be electrically stimulated with the needle assembly to localize the nerve within the tissue. After localizing of the nerve, a focused cold therapy may be delivered to the nerve with the needle assembly. During delivery of the focused cold therapy, the nerve may be electrically stimulated with the needle assembly. An activity of the nerve during the delivery of the focused cold therapy may be sensed for feedback on the delivery of the focused cold therapy to the nerve.

In some embodiments, the method may include coupling an input associated with an electrical nerve stimulation generator to an electrical port to electrically couple the electrical nerve stimulation generator and the needle assembly.

Optionally, coupling the input associated with the electrical nerve stimulation generator to the electrical port may comprise coupling the input associated with the electrical nerve stimulation generator to an electrical port of the needle assembly.

In certain embodiments, coupling the input associated with the electrical nerve stimulation generator to the electrical port may comprise coupling the input associated with the electrical nerve stimulation generator to an electrical port disposed on a handle supporting the needle assembly.

In some embodiments, the method may further include coupling the needle assembly to an adapter of a treatment device handle. Coupling the needle assembly to the adapter of the treatment device handle may electrically couple an electrical nerve stimulation generator housed in the treatment device handle to one or more needles of the needle assembly.

In some embodiments, the needle assembly may electrically stimulate the nerve and may deliver the focused cold therapy with the same needle.

Optionally, the needle of the needle assembly that electrically stimulates the nerve and delivers the focused cold therapy may have a length between 5-20 cm and a blunt distal tip.

In some embodiments, the needle assembly may electrically stimulate the nerve and deliver the focused cold therapy with different needles of the needle assembly. The needle assembly may electrically stimulate the nerve and deliver the focused cold therapy with different needles of the needle assembly. In some embodiments, the needle assembly may include at least a first needle and a second needle adjacent the first needle. The first needle may electrically stimulate the target nerve and the second needle may act as an electrical ground during electrical stimulation of the nerve by the first needle. Optionally, the needle assembly may include a center needle and needles adjacent to the center needle. The target nerve may be electrically stimulated by the center needle and the focused cold therapy may be delivered by the needles adjacent to the center needle. In still further embodiments, the focused cold therapy may be delivered by the needles adjacent to the center needle and the center needle.

In yet another embodiment, a cooling treatment device may be provided with a first needle having a proximal end and a distal end and a length therebetween and a second needle having a proximal end and a distal end and a length therebetween. The first needle may be electrically conductive and the proximal end of the first needle may be coupled with an electrical nerve stimulation generator that generates an electrical field about the distal end of the first needle for nerve stimulation. The second needle may act as an electrical ground during nerve stimulation. At least one of the first needle and the second needle may be configured to produce a cold zone for focused cold therapy.

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim.

The invention will be better understood on reading the following description and examining the figures that accompany it. These figures are provided by way of illustration only and are in no way limiting on the invention.

BRIEF DESCRIPTION OF THE DRAWINGS

Further details, aspects and embodiments of the invention will be described by way of example only and with reference to the drawings. In the drawings, like reference numbers are used to identify like or functionally similar elements. Elements in the figures are illustrated for simplicity and clarity and have not necessarily been drawn to scale.

FIGS. 3A-3E illustrate exemplary embodiments of needle probes, according to some embodiments of the invention;

FIGS. 6-9 illustrate exemplary embodiments of cryofluid delivery tubes, according to some embodiments of the invention;

FIG. 10 illustrates an example of blunt tipped cryoprobe, according to some embodiments of the invention;

FIGS. 11 and 12 illustrate exemplary actuatable cryoprobes, according to some embodiments of the invention;

DETAILED DESCRIPTION

The present invention provides improved medical devices, systems, and methods. Embodiments of the invention may treat target tissues disposed at and below the skin, optionally to treat pain associated with a sensory nerve. In some embodiments, systems, devices, and methods of the present disclosure may utilize an integrated nerve stimulation device for localization of a target nerve.

Embodiments of the invention may utilize a handheld refrigeration system that can use a commercially available cartridge of fluid refrigerant. Refrigerants well suited for use in handheld refrigeration systems may include nitrous oxide and carbon dioxide. These can achieve temperatures approaching −90° C.

Sensory nerves and associated tissues may be temporarily impaired using moderately cold temperatures of 10° C. to −5° C. without permanently disabling the tissue structures. Using an approach similar to that employed for identifying structures associated with atrial fibrillation or for peripheral nerve blocks, a needle probe or other treatment device can be used to identify a target tissue structure in a diagnostic mode with these moderate temperatures, and the same probe (or a different probe) can also be used to provide a longer term or permanent treatment, optionally by treating the target tissue zone and/or inducing apoptosis at temperatures from about −5° C. to about −50° C. In some embodiments, apoptosis may be induced using treatment temperatures from about −1° C. to about −15° C., or from about −1° C. to about −19° C., optionally so as to provide a longer lasting treatment that limits or avoids inflammation and mobilization of skeletal muscle satellite repair cells. In some embodiments, axonotmesis with Wallerian degeneration of a sensory nerve is desired, which may be induced using treatment temperatures from about −20° C. to about −100° C. Hence, the duration of the treatment efficacy of such subdermal cryogenic treatments may be selected and controlled, with colder temperatures, longer treatment times, and/or larger volumes or selected patterns of target tissue determining the longevity of the treatment. Additional description of cryogenic cooling methods and devices may be found in commonly assigned U.S. Pat. No. 7,713,266 entitled "Subdermal Cryogenic Remodeling of Muscle, Nerves, Connective Tissue, and/or Adipose Tissue (Fat)"; U.S. Pat. No. 7,850,683 entitled "Subdermal Cryogenic Remodeling of Muscles, Nerves, Connective Tissue, and/or Adipose Tissue (Fat)"; U.S. Pat. No. 9,039,688 entitled "Method for Reducing Hyperdynamic Facial Wrinkles"; and U.S. Pat. No. 8,298,216 entitled "Pain Management Using Cryogenic Remodeling," the full disclosures of which are each incorporated by reference herein.

Figure 1A:
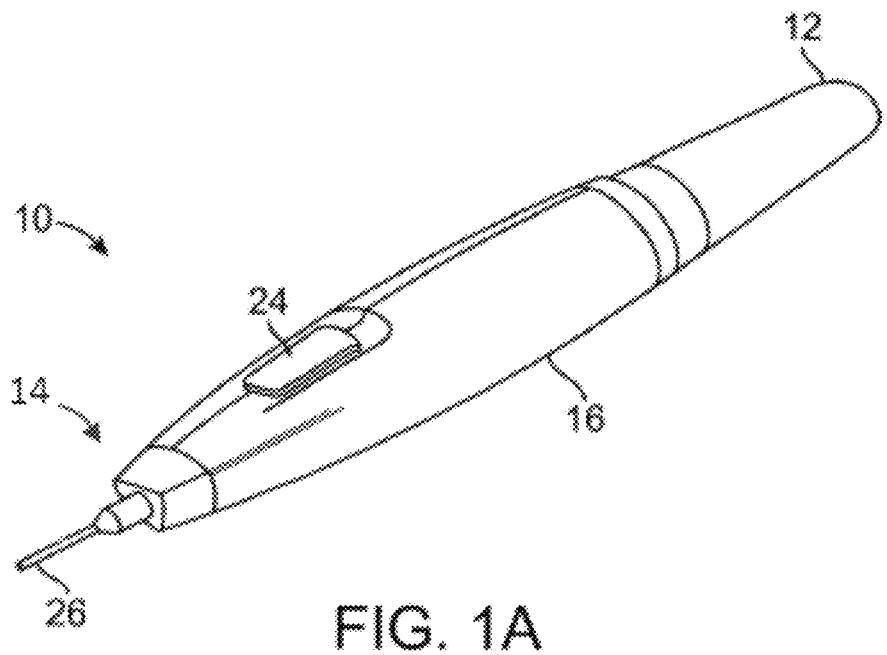
FIG. 1A is a perspective view of a self-contained subdermal cryogenic probe and system, according to some embodiments of the invention.
Figure 1B:
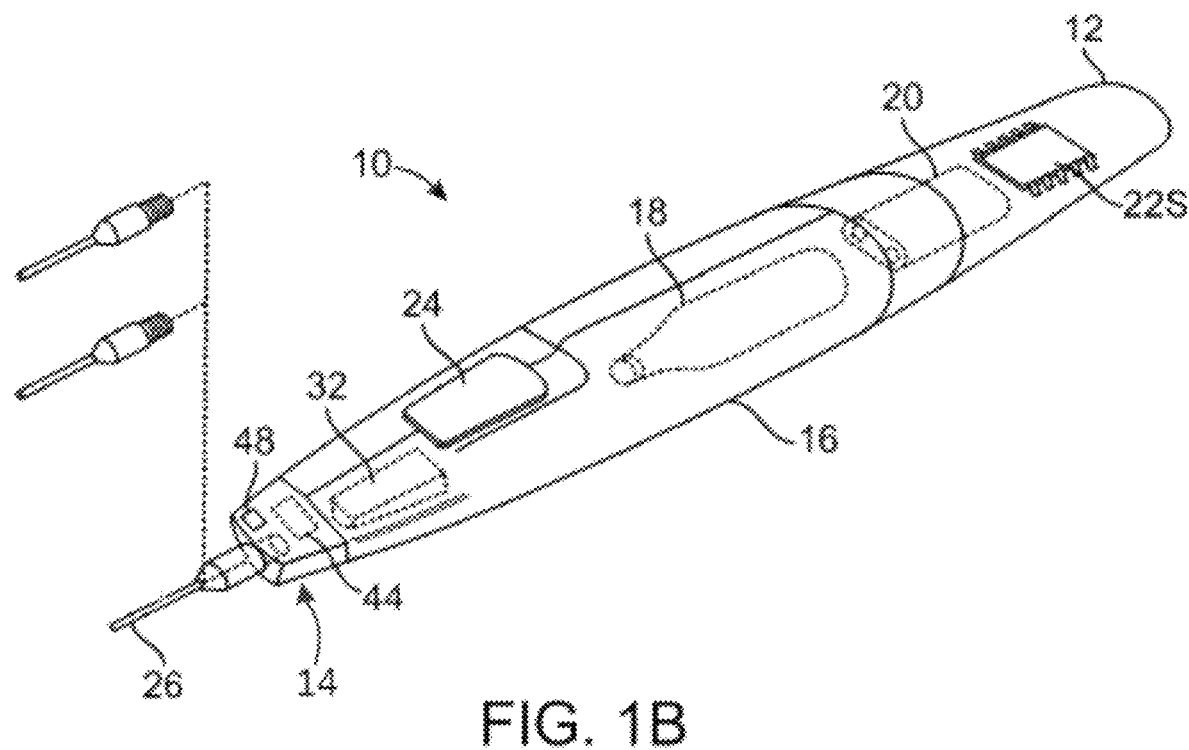
FIG. 1B is a partially transparent perspective view of the self-contained probe of FIG. 1A, showing internal components of the cryogenic system and schematically illustrating replacement treatment needles for use with the disposable probe according to some embodiments of the invention.

Referring now to FIGS. 1A and 1B, a system for cryogenic remodeling here comprises a self-contained probe handpiece generally having a proximal end 12 and a distal end 14. A handpiece body or housing 16 has a size and ergonomic shape suitable for being grasped and supported in a surgeon's hand or other system operator. As can be seen most clearly in FIG. 1B, a cryogenic cooling fluid supply 18, a supply valve 32 and electrical power source 20 are found within housing 16, along with a circuit 22S having a processor for controlling cooling applied by self-contained system 10 in response to actuation of an input 24. Alternatively, electrical power can be applied through a cord from a remote power source. Power source 20 also supplies power to heater element 44 in order to heat the proximal region of probe 26 which may thereby help to prevent unwanted skin damage, and a temperature sensor 48 adjacent the proximal region of probe 26 helps monitor probe temperature. Additional details on the heater 44 and temperature sensor 48 are described in greater detail below. When actuated, supply valve 32 controls the flow of cryogenic cooling fluid from fluid supply 18. Some embodiments may, at least in part, be manually activated, such as through the use of a manual supply valve and/or the like, so that processors, electrical power supplies, and the like may not be required.

Extending distally from distal end 14 of housing 16 may be a tissue-penetrating cryogenic cooling probe 26. Probe 26 is thermally coupled to a cooling fluid path extending from cooling fluid source 18, with the exemplary probe comprising a tubular body receiving at least a portion of the cooling fluid from the cooling fluid source therein. The exemplary probe 26 may comprise a 30 G needle having a sharpened distal end that is axially sealed. Probe 26 may have an axial length between distal end 14 of housing 16 and the distal end of the needle of between about 0.5 mm and 15 cm. Such needles may comprise a stainless steel tube with an inner diameter of about 0.006 inches and an outer diameter of about 0.012 inches, while alternative probes may comprise structures having outer diameters (or other lateral cross-sectional dimensions) from about 0.006 inches to about 0.100 inches. Generally, needle probe 26 may comprise a 16 GA or smaller size needle, often comprising a 20 GA needle or smaller, typically comprising a 25, 26, 27, 28, 29, or 30 GA or smaller needle.

In some embodiments, probe 26 may comprise two or more needles arranged in a linear array, such as those disclosed in previously incorporated U.S. Pat. No. 7,850,683. Another exemplary embodiment of a probe having multiple needle probe configurations allow the cryogenic treatment to be applied to a larger or more specific treatment area. Other needle configurations that facilitate controlling the depth of needle penetration and insulated needle embodiments are disclosed in commonly assigned U.S. Pat. No. 8,409,185 entitled "Replaceable and/or Easily Removable Needle Systems for Dermal and Transdermal Cryogenic Remodeling," the entire content of which is incorporated herein by reference. Multiple needle arrays may also be arrayed in alternative configurations such as a triangular or square array.

Arrays may be designed to treat a particular region of tissue, or to provide a uniform treatment within a particular region, or both. In some embodiments needle 26 may be releasably coupled with body 16 so that it may be replaced after use with a sharper needle (as indicated by the dotted line) or with a needle having a different configuration. In exemplary embodiments, the needle may be threaded into the body, press fit into an aperture in the body or have a quick disconnect such as a detent mechanism for engaging the needle with the body. A quick disconnect with a check valve may be advantageous since it may permit decoupling of the needle from the body at any time without excessive coolant discharge. This can be a useful safety feature in the event that the device fails in operation (e.g., valve failure), allowing an operator to disengage the needle and device from a patient's tissue without exposing the patient to coolant as the system depressurizes. This feature may also be advantageous because it allows an operator to easily exchange a dull needle with a sharp needle in the middle of a treatment. One of skill in the art will appreciate that other coupling mechanisms may be used.

Addressing some of the components within housing 16, the exemplary cooling fluid supply 18 may comprise a canister, sometimes referred to herein as a cartridge, containing a liquid under pressure, with the liquid preferably having a boiling temperature of less than 37° C. at one atmosphere of pressure. When the fluid is thermally coupled to the tissue-penetrating probe 26, and the probe is positioned within the patient so that an outer surface of the probe is adjacent to a target tissue, the heat from the target tissue evaporates at least a portion of the liquid and the enthalpy of vaporization cools the target tissue. A supply valve 32 may be disposed along the cooling fluid flow path between canister 18 and probe 26, or along the cooling fluid path after the probe so as to limit coolant flow thereby regulating the temperature, treatment time, rate of temperature change, or other cooling characteristics. The valve will often be powered electrically via power source 20, per the direction of processor 22, but may at least in part be manually powered. The exemplary power source 20 comprises a rechargeable or single-use battery. Additional details about valve 32 are disclosed below and further disclosure on the power source 20 may be found in commonly assigned Int'l Pub. No. WO 2010/075438 entitled "Integrated Cryosurgical Probe Package with Fluid Reservoir and Limited Electrical Power Source," the entire contents of which are incorporated herein by reference.

The exemplary cooling fluid supply 18 may comprise a single-use canister. Advantageously, the canister and cooling fluid therein may be stored and/or used at (or even above) room temperature. The canister may have a frangible seal or may be refillable, with the exemplary canister containing liquid nitrous oxide, N2O. A variety of alternative cooling fluids might also be used, with exemplary cooling fluids including fluorocarbon refrigerants and/or carbon dioxide. The quantity of cooling fluid contained by canister 18 will typically be sufficient to treat at least a significant region of a patient, but will often be less than sufficient to treat two or more patients. An exemplary liquid N2O canister might contain, for example, a quantity in a range from about 1 gram to about 40 grams of liquid, more preferably from about 1 gram to about 35 grams of liquid, and even more preferably from about 7 grams to about 30 grams of liquid.

Processor 22 will typically comprise a programmable electronic microprocessor embodying machine readable computer code or programming instructions for implementing one or more of the treatment methods described herein. The microprocessor will typically include or be coupled to a memory (such as a non-volatile memory, a flash memory, a read-only memory ("ROM"), a random access memory ("RAM"), or the like) storing the computer code and data to be used thereby, and/or a recording media (including a magnetic recording media such as a hard disk, a floppy disk, or the like; or an optical recording media such as a CD or DVD) may be provided. Suitable interface devices (such as digital-to-analog or analog-to-digital converters, or the like) and input/output devices (such as USB or serial I/O ports, wireless communication cards, graphical display cards, and the like) may also be provided. A wide variety of commercially available or specialized processor structures may be used in different embodiments, and suitable processors may make use of a wide variety of combinations of hardware and/or hardware/software combinations. For example, processor 22 may be integrated on a single processor board and may run a single program or may make use of a plurality of boards running a number of different program modules in a wide variety of alternative distributed data processing or code architectures.

Figure 2A:
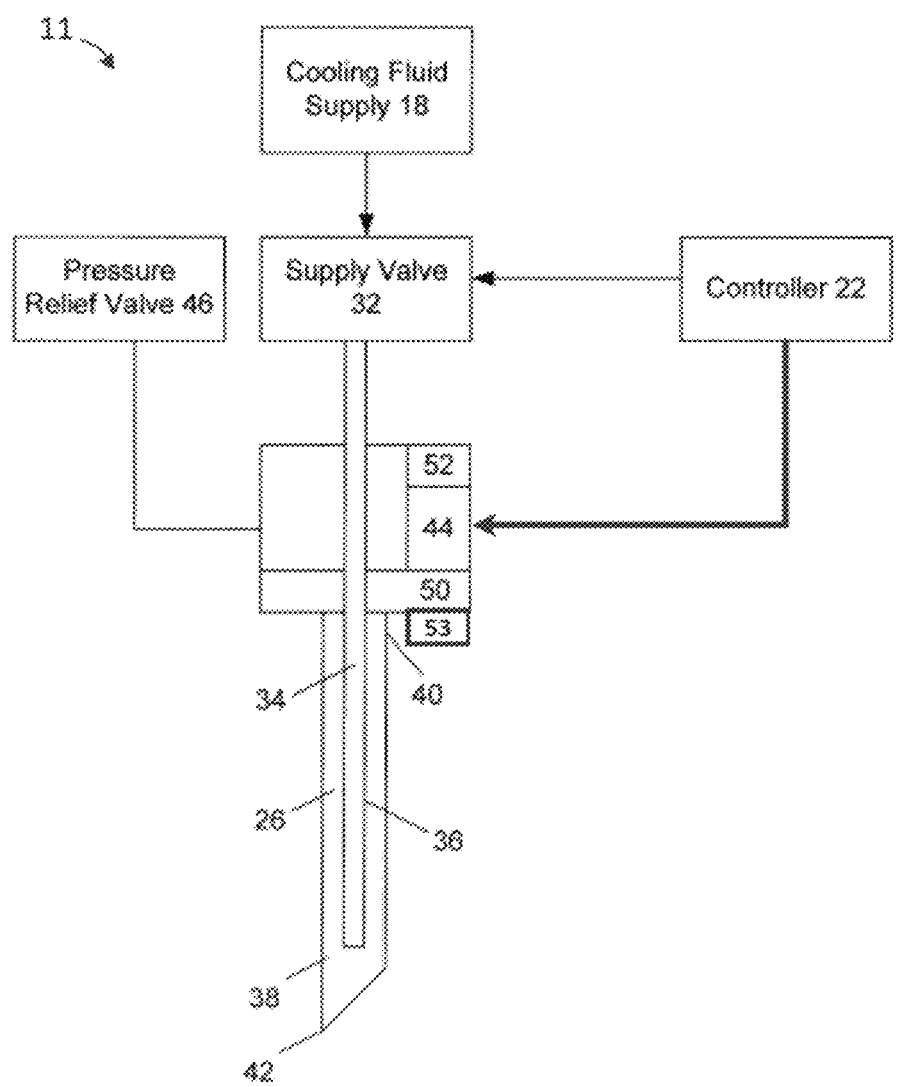
FIG. 2A schematically illustrates exemplary components that may be included in the treatment system.

Referring now to FIG. 2A, schematic 11 shows a simplified diagram of cryogenic cooling fluid flow and control. The flow of cryogenic cooling fluid from fluid supply 18 may be controlled by a supply valve 32. Supply valve 32 may comprise an electrically actuated solenoid valve, a motor actuated valve or the like operating in response to control signals from controller 22, and/or may comprise a manual valve. Exemplary supply valves may comprise structures suitable for on/off valve operation, and may provide venting of the fluid source and/or the cooling fluid path downstream of the valve when cooling flow is halted so as to limit residual cryogenic fluid vaporization and cooling. Additionally, the valve may be actuated by the controller in order to modulate coolant flow to provide high rates of cooling in some instances where it is desirable to promote necrosis of tissue such as in malignant lesions and the like or slow cooling which promotes ice formation between cells rather than within cells when necrosis is not desired. More complex flow modulating valve structures might also be used in other embodiments. For example, other applicable valve embodiments are disclosed in previously incorporated U.S. Pat. No. 8,409,185.

Still referring to FIG. 2A, an optional heater (not illustrated) may be used to heat cooling fluid supply 18 so that heated cooling fluid flows through valve 32 and through a lumen 34 of a cooling fluid supply tube 36. In some embodiments a safety mechanism can be included so that the cooling supply is not overheated. Examples of such embodiments are disclosed in commonly assigned International Publication No. WO 2010075438, the entirety of which is incorporated by reference herein.

Supply tube 36 is, at least in part, disposed within a lumen 38 of needle 26, with the supply tube extending distally from a proximal end 40 of the needle toward a distal end 42. The exemplary supply tube 36 comprises a fused silica tubular structure (not illustrated) having a polymer coating and extending in cantilever into the needle lumen 38. Supply tube 36 may have an inner lumen with an effective inner diameter of less than about 200 µm, the inner diameter often being less than about 100 µm, and typically being less than about 40 µm. Exemplary embodiments of supply tube 36 have inner lumens of between about 15 and 50 µm, such as about 30 µm. An outer diameter or size of supply tube 36 will typically be less than about 1000 µm, often being less than about 800 µm, with exemplary embodiments being between about 60 and 150 µm, such as about 90 µm or 105 µm. The tolerance of the inner lumen diameter of supply tubing 36 will preferably be relatively tight, typically being about +/−10 µm or tighter, often being +/−5 µm or tighter, and ideally being +/−3 µm or tighter (e.g., +/−1 µm), as the small diameter supply tube may provide the majority of (or even substantially all of) the metering of the cooling fluid flow into needle 26. Additional details on various aspects of needle 26 along with alternative embodiments and principles of operation are disclosed in greater detail in U.S. Pat. No. 9,254,162 entitled "Dermal and Transdermal Cryogenic Microprobe Systems and Methods," the entire contents of which are incorporated herein by reference. Previously incorporated U.S. Pat. No. 8,409,185 also discloses additional details on the needle 26 along with various alternative embodiments and principles of operation.

The cooling fluid injected into lumen 38 of needle 26 will typically comprise liquid, though some gas may also be injected. At least some of the liquid vaporizes within needle 26, and the enthalpy of vaporization cools the needle and also the surrounding tissue engaged by the needle. An optional heater 44 (illustrated in FIG. 1B) may be used to heat the proximal region of the needle in order to prevent unwanted skin damage in this area, as discussed in greater detail below. Controlling a pressure of the gas/liquid mixture within needle 26 substantially controls the temperature within lumen 38, and hence the treatment temperature range of the tissue. A relatively simple mechanical pressure relief valve 46 may be used to control the pressure within the lumen of the needle, with the exemplary valve comprising a valve body such as a ball bearing, urged against a valve seat by a biasing spring. An exemplary relief valve is disclosed in U.S. Provisional Patent Application No. 61/116,050 previously incorporated herein by reference. Thus, the relief valve may allow better temperature control in the needle, minimizing transient temperatures. Further details on exhaust volume are disclosed in previously incorporated U.S. Pat. No. 8,409,185.

The heater 44 may be thermally coupled to a thermally responsive element 50, which is supplied with power by the controller 22 and thermally coupled to a proximal portion of the needle 26. The thermally responsive element 50 can be a block constructed from a material of high thermal conductivity and low heat capacity, such as aluminum. A first temperature sensor 52 (e.g., thermistor, thermocouple) can also be thermally coupled the thermally responsive element 50 and communicatively coupled to the controller 22. A second temperature sensor 53 can also be positioned near the heater 44, for example, such that the first temperature sensor 52 and second temperature sensor 53 are placed in different positions within the thermally responsive element 50. In some embodiments, the second temperature sensor 53 is placed closer to a tissue contacting surface than the first temperature sensor 52 is placed in order to provide comparative data (e.g., temperature differential) between the sensors 52, 53. The controller 22 can be configured to receive temperature information of the thermally responsive element 50 via the temperature sensor 52 in order to provide the heater 44 with enough power to maintain the thermally responsive element 50 at a particular temperature.

The controller 22 can be further configured to monitor power draw from the heater 44 in order to characterize tissue type, perform device diagnostics, and/or provide feedback for a tissue treatment algorithm. This can be advantageous over monitoring temperature alone, since power draw from the heater 44 can vary greatly while temperature of the thermally responsive element 50 remains relatively stable. For example, during treatment of target tissue, maintaining the thermally responsive element 50 at 40° C. during a cooling cycle may take 1.0 W initially (for a needle <10 mm in length) and is normally expected to climb to 1.5 W after 20 seconds, due to the needle 26 drawing in surrounding heat. An indication that the heater is drawing 2.0 W after 20 seconds to maintain 40° C. can indicate that an aspect of the system 10 is malfunctioning and/or that the needle 26 is incorrectly positioned. Correlations with power draw and correlated device and/or tissue conditions can be determined experimentally to determine acceptable treatment power ranges.

In some embodiments, it may be preferable to limit frozen tissue that is not at the treatment temperature, i.e., to limit the size of a formed cooling zone within tissue. Such cooling zones may be associated with a particular physical reaction, such as the formation of an ice-ball, or with a particular temperature profile or temperature volume gradient required to therapeutically affect the tissue therein. To achieve this, metering coolant flow could maintain a large thermal gradient at its outside edges. This may be particularly advantageous in applications for creating an array of connected cooling zones (i.e., fence) in a treatment zone, as time would be provided for the treatment zone to fully develop within the fenced in portion of the tissue, while the outer boundaries maintained a relatively large thermal gradient due to the repeated application and removal of refrigeration power. This could provide a mechanism within the body of tissue to thermally regulate the treatment zone and could provide increased ability to modulate the treatment zone at a prescribed distance from the surface of the skin. A related treatment algorithm could be predefined, or it could be in response to feedback from the tissue.

Such feedback could be temperature measurements from the needle 26, or the temperature of the surface of the skin could be measured. However, in many cases monitoring temperature at the needle 26 is impractical due to size constraints. To overcome this, operating performance of the sensorless needle 26 can be interpolated by measuring characteristics of thermally coupled elements, such as the thermally responsive element 50.

Additional methods of monitoring cooling and maintaining an unfrozen portion of the needle include the addition of a heating element and/or monitoring element into the needle itself. This could consist of a small thermistor or thermocouple, and a wire that could provide resistive heat. Other power sources could also be applied such as infrared light, radiofrequency heat, and ultrasound. These systems could also be applied together dependent upon the control of the treatment zone desired.

Alternative methods to inhibit excessively low transient temperatures at the beginning of a refrigeration cycle might be employed instead of or together with the limiting of the exhaust volume. For example, the supply valve 32 might be cycled on and off, typically by controller 22, with a timing sequence that would limit the cooling fluid flowing so that only vaporized gas reached the needle lumen 38 (or a sufficiently limited amount of liquid to avoid excessive dropping of the needle lumen temperature). This cycling might be ended once the exhaust volume pressure was sufficient so that the refrigeration temperature would be within desired limits during steady state flow. Analytical models that may be used to estimate cooling flows are described in greater detail in previously incorporated U.S. Pat. No. 9,254,162.

Figure 2B:
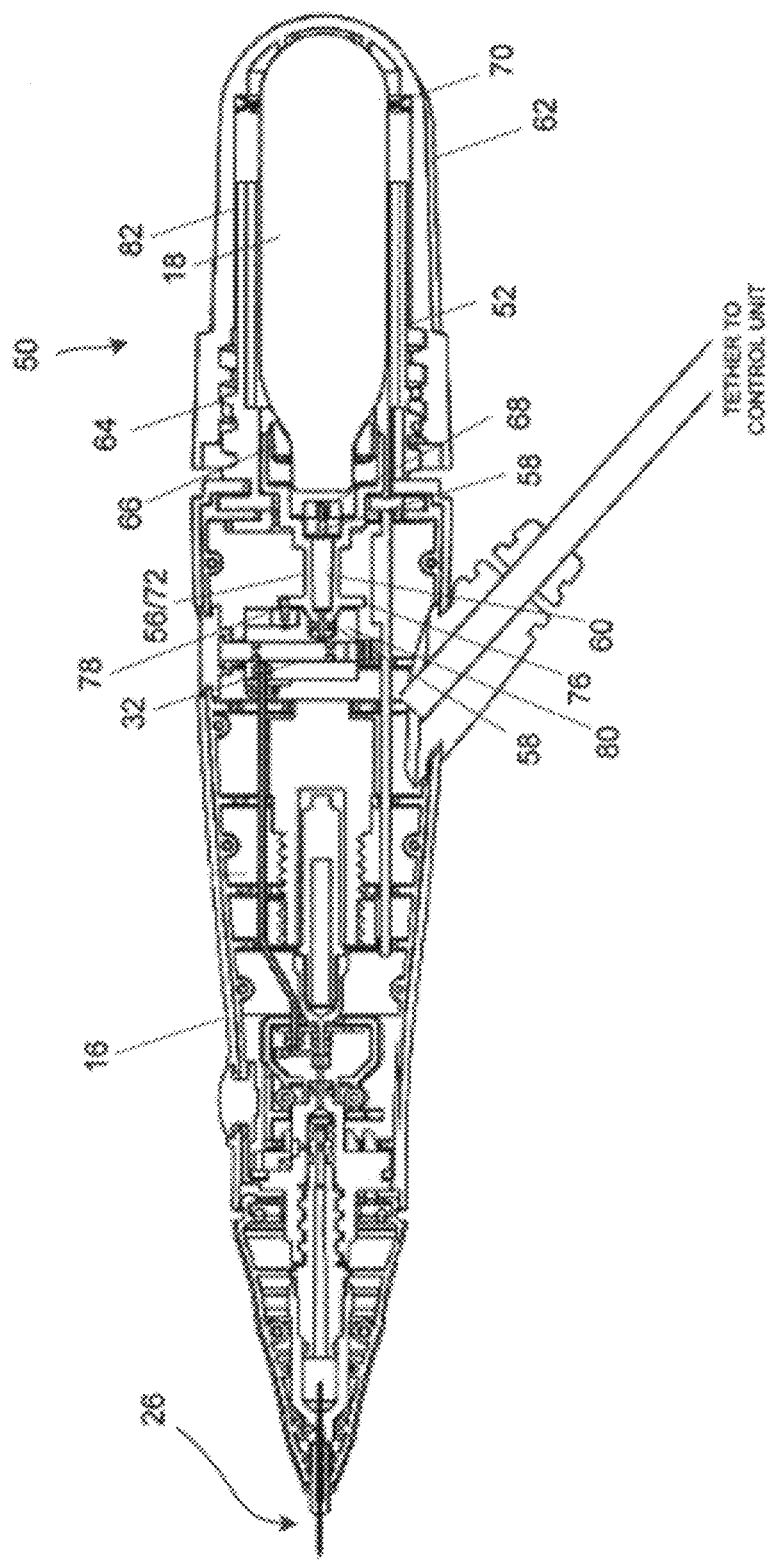
FIG. 2B is a cross-sectional view of the system of FIG. 1A, according to some embodiments of the invention.

FIG. 2B shows a cross-section of the housing 16. This embodiment of the housing 16 may be powered by an external source, hence the attached cable, but could alternatively include a portable power source. As shown, the housing includes a cartridge holder 50. The cartridge holder 50 includes a cartridge receiver 52, which may be configured to hold a pressured refrigerant cartridge 18. The cartridge receiver 52 includes an elongated cylindrical passage 70, which is dimensioned to hold a commercially available cooling fluid cartridge 18. A distal portion of the cartridge receiver 52 includes a filter device 56, which has an elongated conical shape. In some embodiments, the cartridge holder 50 may be largely integrated into the housing 16 as shown, however, in alternative embodiments, the cartridge holder 50 is a wholly separate assembly, which may be pre-provided with a coolant fluid source 18.

The filter device 56 may fluidly couple the coolant fluid source (cartridge) 18 at a proximal end to the valve 32 at a distal end. The filter device 56 may include at least one particulate filter 58. In the shown embodiment, a particulate filter 58 at each proximal and distal end of the filter device 56 may be included. The particulate filter 58 can be configured to prevent particles of a certain size from passing through. For example, the particulate filter 58 can be constructed as a microscreen having a plurality of passages less than 2 microns in width, and thus particles greater than 2 microns would not be able to pass.

The filter device 56 also includes a molecular filter 60 that is configured to capture fluid impurities. In some embodiments, the molecular filter 60 is a plurality of filter media (e.g., pellets, powder, particles) configured to trap molecules of a certain size. For example, the filter media can comprise molecular sieves having pores ranging from 1-20 Å. In another example, the pores have an average size of 5 Å. The molecular filter 60 can have two modalities. In a first mode, the molecular filter 60 will filter fluid impurities received from the cartridge 18. However, in another mode, the molecular filter 60 can capture impurities within the valve 32 and fluid supply tube 36 when the system 10 is not in use, i.e., when the cartridge 18 is not fluidly connected to the valve 32.

Alternatively, the filter device 56 can be constructed primarily from ePTFE (such as a GORE material), sintered polyethylene (such as made by POREX), or metal mesh. The pore size and filter thickness can be optimized to minimize pressure drop while capturing the majority of contaminants. These various materials can be treated to make it hydrophobic (e.g., by a plasma treatment) and/or oleophobic so as to repel water or hydrocarbon contaminants.

It has been found that in some instances fluid impurities may leach out from various aspects of the system 10. These impurities can include trapped moisture in the form of water molecules and chemical gasses. The presence of these impurities is believed to hamper cooling performance of the system 10. The filter device 56 can act as a desiccant that attracts and traps moisture within the system 10, as well as chemicals out gassed from various aspects of the system 10. Alternately the various aspects of the system 10 can be coated or plated with impermeable materials such as a metal.

Figure 2C:
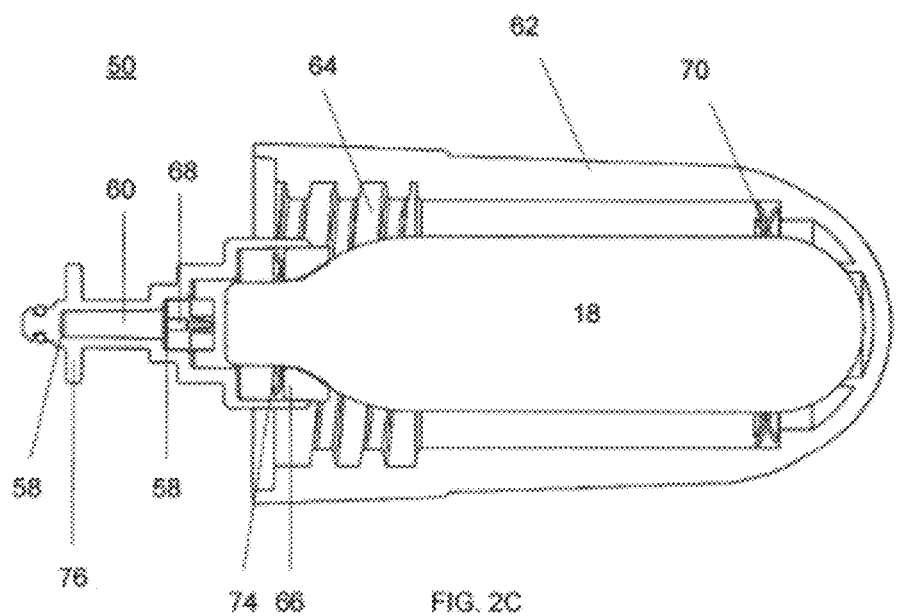
FIGS. 2C and 2D are cross-sectional views showing exemplary operational configurations of a portion of the system of FIG. 2B.
Figure 2D:
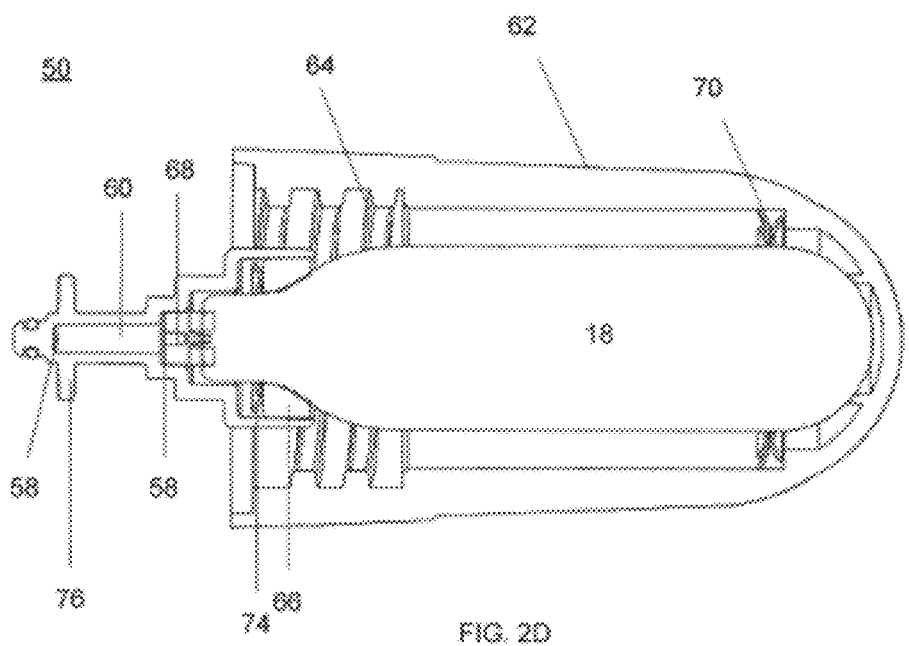

As shown in FIG. 2B and in more detail in FIG. 2C and FIG. 2D, the cartridge 18 can be held by the cartridge receiver 52 such that the cartridge 18 remains intact and unpunctured. In this inactive mode, the cartridge may not be fluidly connected to the valve 32. A removable cartridge cover 62 can be attached to the cartridge receiver 52 such that the inactive mode is maintained while the cartridge is held by the system 10.

In use, the cartridge cover 62 can be removed and supplied with a cartridge containing a cooling fluid. The cartridge cover 62 can then be reattached to the cartridge receiver 52 by turning the cartridge cover 62 until female threads 64 of the cartridge cover 62 engage with male threads of the cartridge receiver 52. The cartridge cover 62 can be turned until resilient force is felt from an elastic seal 66, as shown in FIG. 2C. To place the system 10 into use, the cartridge cover 62 can be further turned until the distal tip of the cartridge 18 is punctured by a puncture pin connector 68, as shown in FIG. 2D. Once the cartridge 18 is punctured, cooling fluid may escape the cartridge by flowing through the filter device 56, where the impurities within the cooling fluid may be captured. The purified cooling fluid then passes to the valve 32, and onto the coolant supply tube 36 to cool the probe 26. In some embodiments the filter device, or portions thereof, may be replaceable.

In some embodiments, the puncture pin connector 68 can have a two-way valve (e.g., ball/seat and spring) that is closed unless connected to the cartridge. Alternately, pressure can be used to open the valve. The valve closes when the cartridge is removed. In some embodiments, there may be a relief valve piloted by a spring which is balanced by high-pressure nitrous when the cartridge is installed and the system is pressurized, but allows the high-pressure cryogen to vent when the cryogen is removed. In addition, the design can include a vent port that vents cold cryogen away from the cartridge port. Cold venting cryogen locally can cause condensation in the form of liquid water to form from the surrounding environment. Liquid water or water vapor entering the system can hamper the cryogenic performance. Further, fluid carrying portions of the cartridge receiver 52 can be treated (e.g., plasma treatment) to become hydrophobic and/or oleophobic so as to repel water or hydrocarbon contaminants.

Figure 3A:
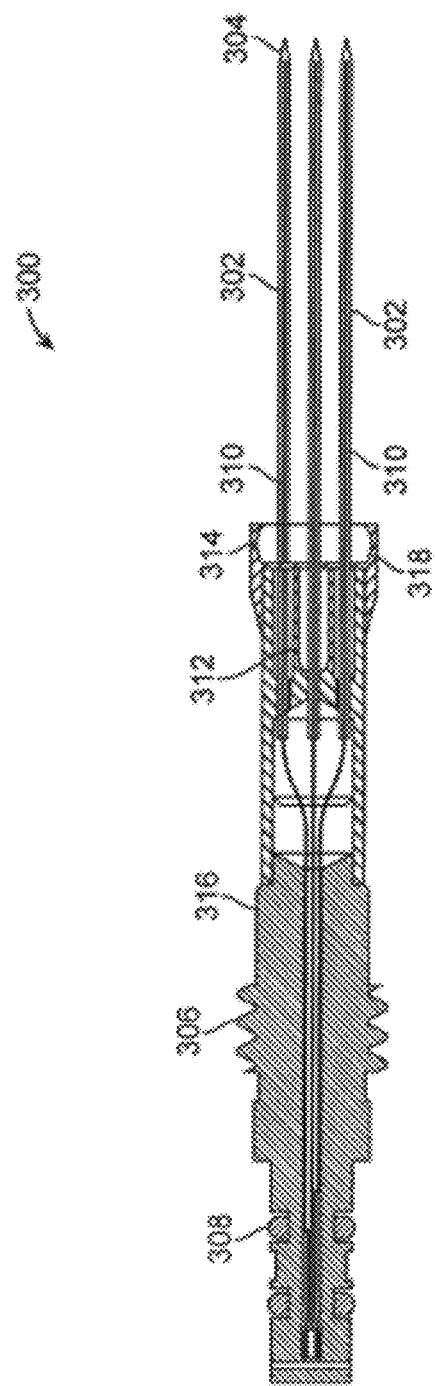

Turning now to FIG. 3A and FIG. 3B, an exemplary embodiment of probe 300 having multiple needles 302 is described. In FIG. 3A, probe housing 316 includes threads 306 that allow the probe to be threadably engaged with the housing 16 of a cryogenic device. O-rings 308 fluidly seal the probe housing 316 with the device housing 16 and prevent coolant from leaking around the interface between the two components. Probe 300 includes an array of three distally extending needle shafts 302, each having a sharpened, tissue penetrating tip 304. In certain embodiments, using three linearly arranged needles allows a greater area of tissue to be treated as compared with a single needle. In use, coolant flows through lumens 310 into the needle shafts 302 thereby cooling the needle shafts 302. Ideally, only the distal portion of the needle shaft 302 would be cooled so that only the target tissue receives the cryogenic treatment. However, as the cooling fluid flows through the probe 300, probe temperature decreases proximally along the length of the needle shafts 302 towards the probe hub 318. The proximal portion of needle shaft 302 and the probe hub 318 contact skin and may become very cold (e.g. −20° C. to −25° C.) and this can damage the skin in the form of blistering or loss of skin pigmentation. Therefore it would be desirable to ensure that the proximal portion of needle shaft 302 and hub 318 remains warmer than the distal portion of needle shaft 302. A proposed solution to this challenge is to include a heater element 314 that can heat the proximal portion of needle shaft 302 and an optional temperature sensor 312 to monitor temperature in this region. To further this, a proximal portion of the needle shaft 302 can be coated with a highly thermally conductive material, e.g., gold, that is conductively coupled to both the needle shaft 302 and heater element 314. Details of this construction are disclosed below.

In the exemplary embodiment of FIG. 3A, resistive heater element 314 is disposed near the needle hub 318 and near a proximal region of needle shaft 302. The resistance of the heater element is preferably 1Ω to 1KΩ, and more preferably from 5Ω to 50Ω. Additionally, a temperature sensor 312 such as a thermistor or thermocouple is also disposed in the same vicinity. Thus, during a treatment as the needles cool down, the heater 314 may be turned on in order to heat the hub 318 and proximal region of needle shaft 302, thereby preventing this portion of the device from cooling down as much as the remainder of the needle shaft 302. The temperature sensor 312 may provide feedback to controller 22 and a feedback loop can be used to control the heater 314. The cooling power of the nitrous oxide may eventually overcome the effects of the heater, therefore the microprocessor may also be programmed with a warning light and/or an automatic shutoff time to stop the cooling treatment before skin damage occurs. An added benefit of using such a heater element is the fact that the heat helps to moderate the flow of cooling fluid into the needle shaft 302 helping to provide more uniform coolant mass flow to the needles shaft 302 with more uniform cooling resulting.

The embodiment of FIG. 3A illustrates a heater fixed to the probe hub. In other embodiments, the heater may float, thereby ensuring proper skin contact and proper heat transfer to the skin. Examples of floating heaters are disclosed in commonly assigned Int'l Pub. No. WO 2010/075448 entitled "Skin Protection for Subdermal Cryogenic Remodeling for Cosmetic and Other Treatments," the entirety of which is incorporated by reference herein.

In this exemplary embodiment, three needles are illustrated. One of skill in the art will appreciate that a single needle may be used, as well as two, four, five, six, or more needles may be used. When a plurality of needles are used, they may be arranged in any number of patterns. For example, a single linear array may be used, or a two dimensional or three dimensional array may be used. Examples of two dimensional arrays include any number of rows and columns of needles (e.g., a rectangular array, a square array, elliptical, circular, triangular, etc.), and examples of three dimensional arrays include those where the needle tips are at different distances from the probe hub, such as in an inverted pyramid shape.

FIG. 3B illustrates a cross-section of the needle shaft 302 of needle probe 300. The needle shaft can be conductively coupled (e.g., welded, conductively bonded, press fit) to a conductive heater 314 to enable heat transfer therebetween. The needle shaft 302 is generally a small (e.g., 20-30 gauge) closed tip hollow needle, which can be between about 0.2 mm and 15 cm, preferably having a length from about 0.3 cm to about 3 cm. The conductive heater element 314 can be housed within a conductive block 315 of high thermally conductive material, such as aluminum and include an electrically insulated coating, such as Type III anodized coating to electrically insulate it without diminishing its heat transfer properties. The conductive block 315 can be heated by a resister or other heating element (e.g., cartridge heater, nichrome wire, etc.) bonded thereto with a heat conductive adhesive, such as epoxy. A thermistor can be coupled to the conductive block 315 with heat conductive epoxy allows temperature monitoring. Other temperature sensors may also be used, such as a thermocouple.

A cladding 320 of conductive material is directly conductively coupled to the proximal portion of the shaft of the needle 302, which can be stainless steel. In some embodiments, the cladding 320 is a layer of gold, or alloys thereof, coated on the exterior of the proximal portion of the needle shaft 302. In some embodiments, the exposed length of cladding 320 on the proximal portion of the needle is 2-100 mm. In some embodiments, the cladding 320 can be of a thickness such that the clad portion has a diameter ranging from 0.017-0.020 in., and in some embodiments 0.0182 in. Accordingly, the cladding 320 can be conductively coupled to the material of the needle 302, which can be less conductive, than the cladding 320. The cladding 320 may modify the lateral force required to deflect or bend the needle 26. Cladding 320 may be used to provide a stiffer needle shaft along the proximal end in order to more easily transfer force to the leading tip during placement and allow the distal portion of the needle to deflect more easily when it is dissecting a tissue interface within the body. The stiffness of needle 26 can vary from one end to the other end by other means such as material selection, metal tempering, variation of the inner diameter of the needle 26, or segments of needle shaft joined together end-to-end to form one contiguous needle 26. In some embodiments, increasing the stiffness of the distal portion of the needle 26 can be used to flex the proximal portion of the needle to access difficult treatment sites as in the case of upper limb spasticity where bending of the needle outside the body may be used to access a target peripheral nerve along the desired tissue plane.

In some embodiments, the cladding 320 can include sub-coatings (e.g., nickel) that promote adhesion of an outer coating that would otherwise not bond well to the needle shaft 302. Other highly conductive materials can be used as well, such as copper, silver, aluminum, and alloys thereof. In some embodiments, a protective polymer or metal coating can cover the cladding to promote biocompatibility of an otherwise non-biocompatible but highly conductive cladding material. Such a biocompatible coating however, would be applied to not disrupt conductivity between the conductive block 315. In some embodiments, an insulating layer, such as a ceramic material, is coated over the cladding 320, which remains conductively coupled to the needle shaft 302.

In use, the cladding 320 can transfer heat to the proximal portion of the needle 302 to prevent directly surrounding tissue from dropping to cryogenic temperatures. Protection can be derived from heating the non-targeting tissue during a cooling procedure, and in some embodiments before the procedure as well. The mechanism of protection may be providing heat to pressurized cryogenic cooling fluid passing within the proximal portion of the needle to affect complete vaporization of the fluid. Thus, the non-target tissue in contact with the proximal portion of the needle shaft 302 does not need to supply heat, as opposed to target tissue in contact with the distal region of the needle shaft 302. To help further this effect, in some embodiments the cladding 320 is coating within the interior of the distal portion of the needle, with or without an exterior cladding. To additionally help further this effect, in some embodiments, the distal portion of the needle can be thermally isolated from the proximal portion by a junction, such as a ceramic junction. While in some further embodiments, the entirety of the proximal portion is constructed from a more conductive material than the distal portion.

In use, it has been determined experimentally that the cladding 320 can help limit formation of a cooling zone to the distal portion of the needle shaft 302, which tends to demarcate at a distal end of the cladding 320. Accordingly, cooling zones are formed only about the distal portions of the needles. Thus, non-target tissue in direct contact with proximal needle shafts remain protected from effects of cryogenic temperatures. Such effects can include discoloration and blistering of the skin. Such cooling zones may be associated with a particular physical reaction, such as the formation of an ice-ball, or with a particular temperature required to therapeutically affect the tissue therein.

Standard stainless steel needles and gold clad steel needles were tested in porcine muscle and fat. Temperatures were recorded measured 2 mm from the proximal end of the needle shafts, about where the cladding distally terminates, and at the distal tip of the needles. Temperatures for clad needles were dramatically warmer at the 2 mm point versus the unclad needles, and did not drop below 4° C. The 2 mm points of the standard stainless steel needles almost equalize in temperature with the distal tip at temperatures below 0° C.

Figure 3C:
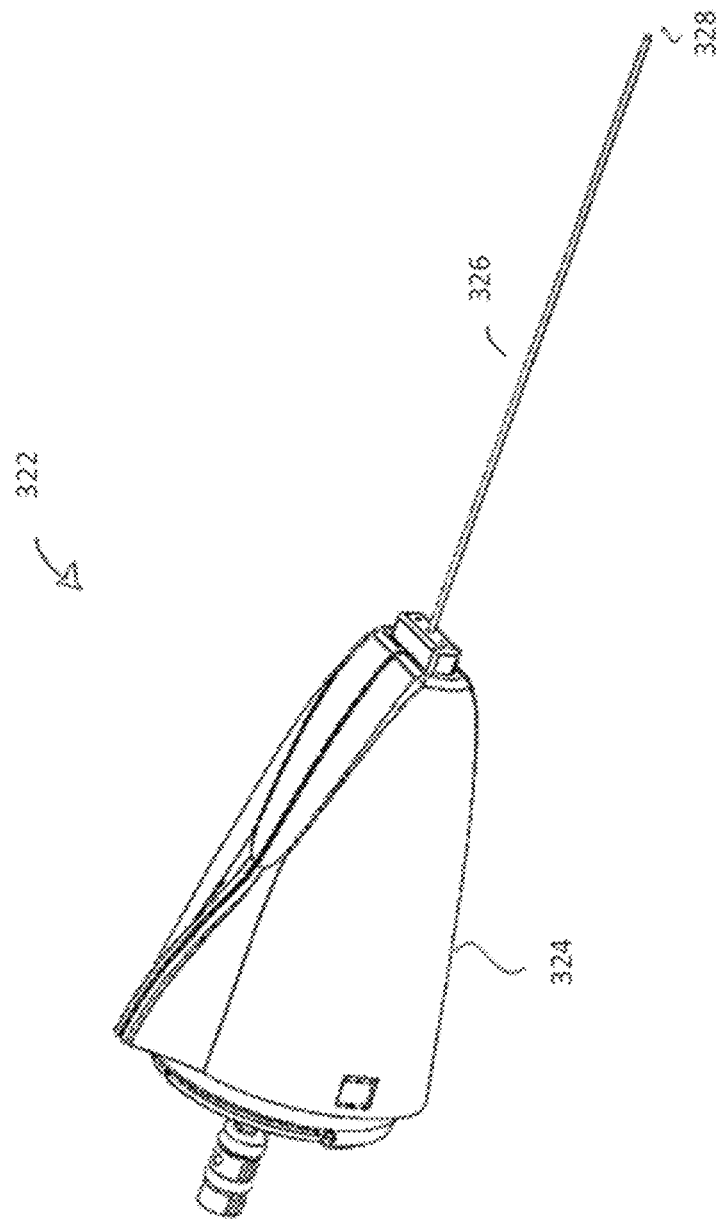

FIGS. 3C and 3D illustrates a detachable probe tip 322 having a hub connector 324 and an elongated probe 326. The probe tip 322 shares much of its construction with probe 300. However, the elongated probe 326 features a blunt tip 328 that is adapted for blunt dissection of tissue. The blunt tip 328 can feature a full radius tip, less than a full radius tip, or conical tip. In some embodiments, a dulled or truncated needle is used. The elongated probe 326 can be 20 gauge or smaller in diameter, and in some embodiments range in size from 25-30 gauge. As with the embodiments described above, an internal supply tube 330 extends in cantilever. However, the exit of the supply tube 330 can be disposed at positions within the elongated probe 326 other than proximate the blunt tip 328. Further, the supply tube 330 can be adapted to create an elongated zone of cooling, e.g., by having multiple exit points for cryofluid to exit from.

The elongated probe 326 and supply tube 330 may be configured to resiliently bend in use, throughout their length at angles approaching 120°, with a 5-10 mm bend radius. This may be very challenging considering the small sizes of the elongated probe 326 and supply tube 330, and also considering that the supply tube 330 is often constructed from fused silica. Accordingly, the elongated probe 326 can be constructed from a resilient material, such as stainless steel, and of a particular diameter and wall thickness [0.004 to 1.0 mm], such that the elongated probe in combination with the supply tube 330 is not overly resilient so as to overtly resist manipulation, but sufficiently strong so as to prevent kinking that can result in coolant escaping. For example, the elongated probe can be 15 gauge or smaller in diameter, even ranging from 20-30 gauge in diameter. The elongated probe can have a very disparate length to diameter ratio, for example, the elongated probe can be greater than 30 mm in length, and in some cases range from 30-100 mm in length. To further the aforementioned goals, the supply tube 330 can include a polymer coating 332, such as a polyimide coating that terminates approximately halfway down its length, to resist kinking and aid in resiliency. The polymer coating 332 can be a secondary coating over a primary polyimide coating that extends fully along the supply tube. However, it should be understood that the coating is not limited to polyimide, and other suitable materials can be used. In some embodiments, the flexibility of the elongated probe 326 will vary from the proximal end to the distal end. For example, by creating certain portions that have more or less flexibility than others. This may be done, for example, by modifying wall thickness, adding material (such as the cladding discussed above), and/or heat treating certain portions of the elongated probe 326 and/or supply tube 330. For example, decreasing the flexibility of elongated probe 326 along the proximal end can improve the transfer of force from the hand piece to the elongated probe end for better feel and easier tip placement for treatment. The elongated probe and supply line 330 may be configured to resiliently bend in use to different degrees along the length at angles approaching 120°, with a varying bend radius as small as 5 mm. In some embodiments, the elongated probe 326 will have external markings along the needle shaft indicating the length of needle inserted into the tissue.

Figure 3E:
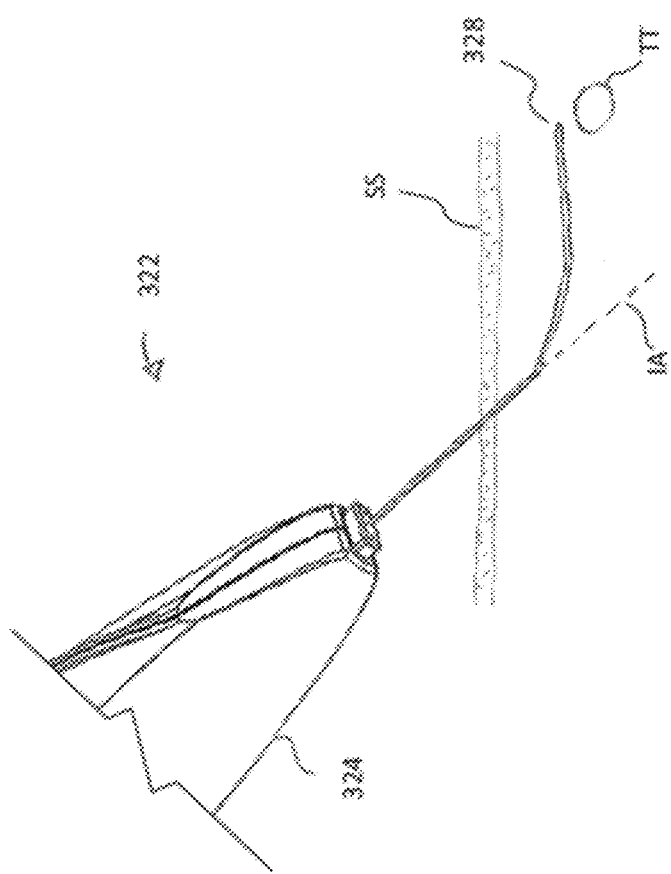

FIG. 3E illustrates an exemplary detachable probe tip 322 inserted through skin surface SS. As illustrated, the probe tip 322 is inserted along an insertion axis IA through the skin surface SS. Thereafter, the needle may be bent away from the insertion axis IA and advanced toward a target tissue TT in order to position blunt tip 328 adjacent to the target tissue TT. In some embodiments, the target tissue may be the infrapatellar branch of the saphenous nerve. In other embodiments the target tissue may be one or more branches of the anterior femoral cutaneous nerve or the lateral femoral cutaneous nerve.

In some embodiments, the probe tip 322 does not include a heating element, such as the heater described with reference to probe 300, since the effective treating portion of the elongated probe 326 (i.e., the area of the elongated probe where a cooling zone emanates from) is well laterally displaced from the hub connector 324 and elongated probe proximal junction. Embodiments of the supply tube are further described below and within commonly assigned U.S. Pub. No. 2012/0089211, which is incorporated by reference.

Figure 4A:
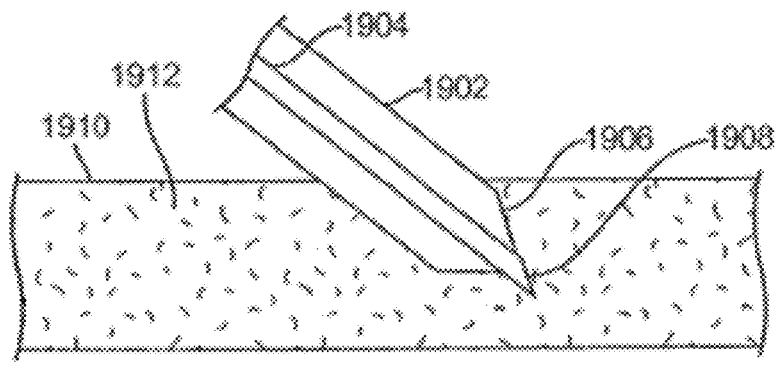
FIGS. 4A-4C illustrate an exemplary method of introducing a cryogenic probe to a treatment area, according to some embodiments of the invention.
Figure 4B:
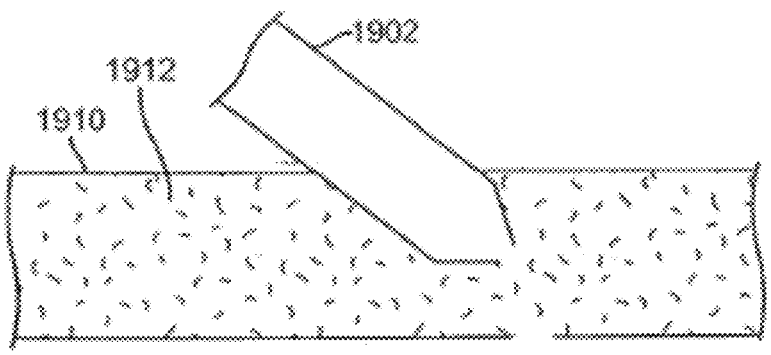
Figure 4C:
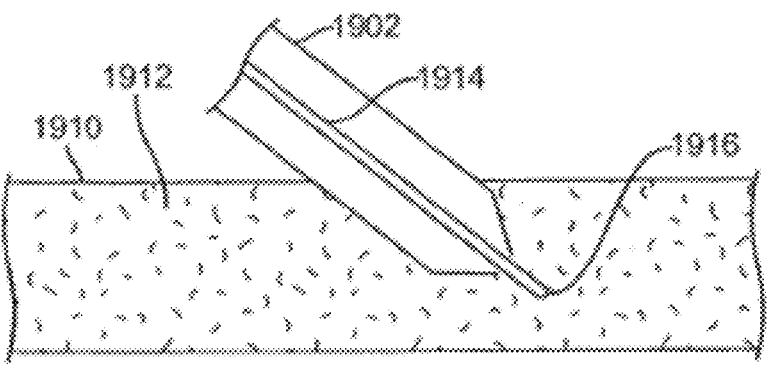

FIGS. 4A-4C illustrate an exemplary method of creating a hole through the skin that allows multiple insertions and positioning of a cryoprobe therethrough. This may be helpful when the needle must be advanced distally past dense scar tissue. In FIG. 4A a cannula or sheath 1902 is disposed over a needle 1904 having a tissue penetrating distal end 1908. The cannula may have a tapered distal portion 1906 to help spread and dilate the skin during insertion. The needle/sheath assembly is then advanced into and pierces the skin 1910 into the desired target tissue 1912. The inner pathway of the cannula or sheath 1902 may be curved to assist in directing the flexible needle 1904, or other probe, into a desired tissue layer coincident with the desired needle path in the tissue. Once the needle/sheath assembly has been advanced to a desired location, the needle 1904 may be proximally retracted and removed from the sheath 1902. The sheath (or introducer) now may be used as an easy way of introducing a cryoprobe through the skin without piercing it, and directing the cryoprobe to the desired target treatment area. FIG. 4B shows the sheath 1902 in position with the needle 1904 removed. FIG. 4C shows insertion of a cryoprobe 1914 into the sheath such that a blunt tip 1916 of the cryoprobe 1914 is adjacent the target treatment tissue. The cryoprobe may then be cooled and the treatment tissue cooled to achieve any of the cosmetic or therapeutic effects discussed above. In this embodiment, the cryoprobe preferably has a blunt tip 1916 in order to minimize tissue trauma. In other embodiments, the tip may be sharp and be adapted to penetrate tissue, or it may be round and spherical. The cryoprobe 1914 may then be at least partially retracted from the sheath 1902 and/or rotated and then re-advanced to the same or different depth and repositioned in sheath 1902 so that the tip engages a different portion of the target treatment tissue without requiring an additional piercing of the skin. The probe angle relative to the tissue may also be adjusted, and the cryoprobe may be advanced and retracted multiple times through the sheath so that the entire target tissue is cryogenically treated.

While the embodiment of FIGS. 4A-4C illustrates a cryoprobe having only a single probe, the cryoprobe may have an array of probes. Any of the cryoprobes described above may be used with an appropriately sized sheath. In some embodiments, the cryoprobe comprises a linear or two dimensional array of probes. Lidocaine or other local anesthetics may be used during insertion of the sheath or cryoprobe in order to minimize patient discomfort. The angle of insertion for the sheath may be anywhere from 0 to 180 degrees relative to the skin surface, and in specific embodiments is 15 to 45 degrees. The sheath may be inserted at any depth, but in specific embodiments of treating lines/wrinkles of the face, the sheath may be inserted to a depth of 1 mm to 10 mm, and more preferably to a depth of 2 mm to 5 mm.

Figure 4D:
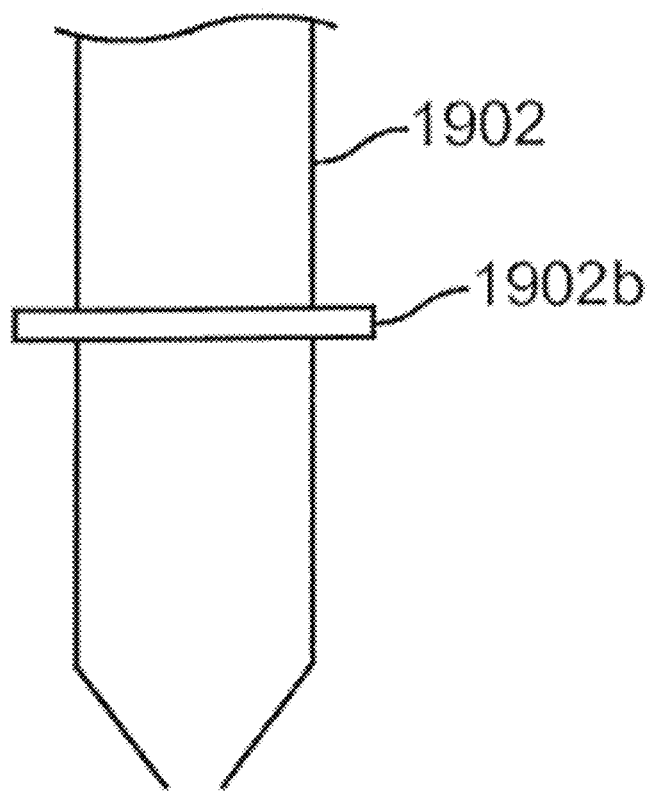
FIG. 4D illustrates an alternative exemplary embodiment of a sheath, according to some embodiments of the invention.

In an alternative embodiment seen in FIG. 4D, the sheath 1902 may include an annular flange 1902b on an outside surface of the sheath in order to serve as a stop so that the sheath is only inserted a preset amount into the tissue. The position of the flange 1902b may be adjustable or fixed. The proximal end of the sheath in this embodiment, or any of the other sheath embodiments may also include a one-way valve such as a hemostasis valve to prevent backflow of blood or other fluids that may exit the sheath. The sheath may also insulate a portion of the cryoprobe and prevent or minimize cooling of unwanted regions of tissue.

Figure 5:
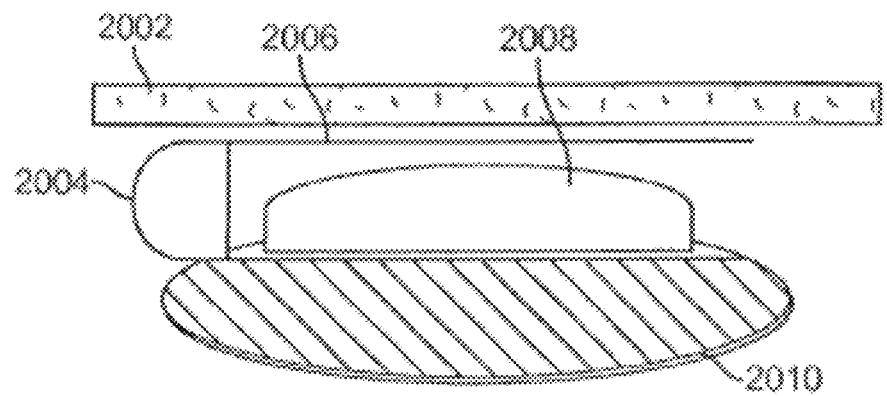
FIG. 5 illustrates an exemplary insulated cryoprobe, according to some embodiments of the invention.

Any of the cryoprobes described above may be used with the sheath embodiment described above (e.g., in FIGS. 3B, 4A-4C). Other cryoprobes may also be used with this sheath embodiment, or they may be used alone, in multi-probe arrays, or combined with other treatments. For example, a portion of the cryoprobe 2006 may be insulated as seen in FIG. 5. Cryoprobe 2006 includes a blunt tip 2004 with an insulated section 2008 of the probe. Thus, when the cryoprobe is disposed in the treatment tissue under the skin 2002 and cooled, the cryoprobe preferentially creates a cooling zone along one side while the other side remains uncooled, or only experiences limited cooling. For example, in FIG. 5, the cooling zone 2010 is limited to a region below the cryoprobe 2006, while the region above the cryoprobe and below the skin 2002 remain unaffected by the cooling.

Figure 6:
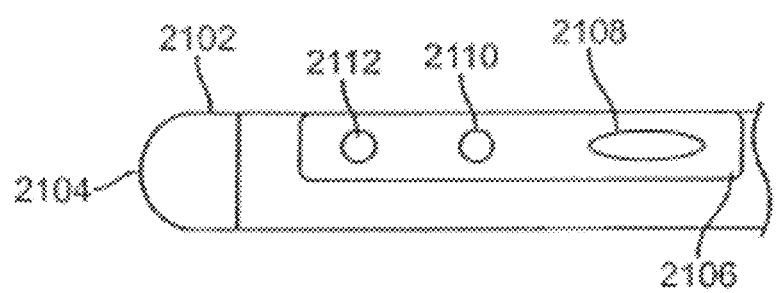
Figure 7:
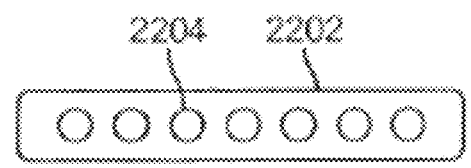

Different zones of cryotherapy may also be created by different geometries of the coolant fluid supply tube that is disposed in the cryoprobe. FIGS. 6-9 illustrate exemplary embodiments of different coolant fluid supply tubes. In FIG. 6 the coolant fluid supply tube 2106 is offset from the central axis of a cryoprobe 2102 having a blunt tip 2104. Additionally, the coolant fluid supply tube 2106 includes several exit ports for the coolant including circular ports 2110, 2112 near the distal end of the coolant fluid supply tube and an elliptical port 2108 proximal of the other ports. These ports may be arranged in varying sizes, and varying geometries in order to control the flow of cryofluid which in turn controls probe cooling of the target tissue. FIG. 7 illustrates an alternative embodiment of a coolant fluid supply tube 2202 having a plurality of circular ports 2204 for controlling cryofluid flow. FIG. 8 illustrates yet another embodiment of a coolant fluid supply tube 2302 having a plurality of elliptical holes 2304, and FIG. 9 shows still another embodiment of a coolant fluid supply tube 2402 having a plurality of ports ranging from smaller diameter circular holes 2404 near the distal end of the supply tube 2402 to larger diameter circular holes 2406 that are more proximally located on the supply tube 2402.

As discussed above, it may be preferable to have a blunt tip on the distal end of the cryoprobe in order to minimize tissue trauma. The blunt tip may be formed by rounding off the distal end of the probe, or a bladder or balloon 2506 may be placed on the distal portion of the probe 2504 as seen in FIG. 10. A filling tube or inflation lumen 2502 may be integral with or separate from the cryoprobe 2504, and may be used to deliver fluid to the balloon to fill the balloon 2506 up to form the atraumatic tip.

In some instances, it may be desirable to provide expandable cryoprobes that can treat different target tissues or accommodate different anatomies. For example, in FIGS. 11 and 12, a pair of cryoprobes 2606 with blunt tips 2604 may be delivered in parallel with one another and in a low profile through a sheath 2602 to the treatment area. Once delivered, the probes may be actuated to separate the tips 2604 from one another, thereby increasing the cooling zone. After the cryotherapy has been administered, the probes may be collapsed back into their low profile configuration, and retracted from the sheath.

In some embodiments, the probe may have a sharp tissue piercing distal tip, and in other embodiments, the probe may have a blunt tip for minimizing tissue trauma. To navigate through tissue, it may be desirable to have a certain column strength for the probe in order to avoid bending, buckling or splaying, especially when the probe comprises two or more probes in an array. One exemplary embodiment may utilize a variable stiff portion of a sleeve along the probe body to provide additional column strength for pushing the probe through tissue.

Figure 13:
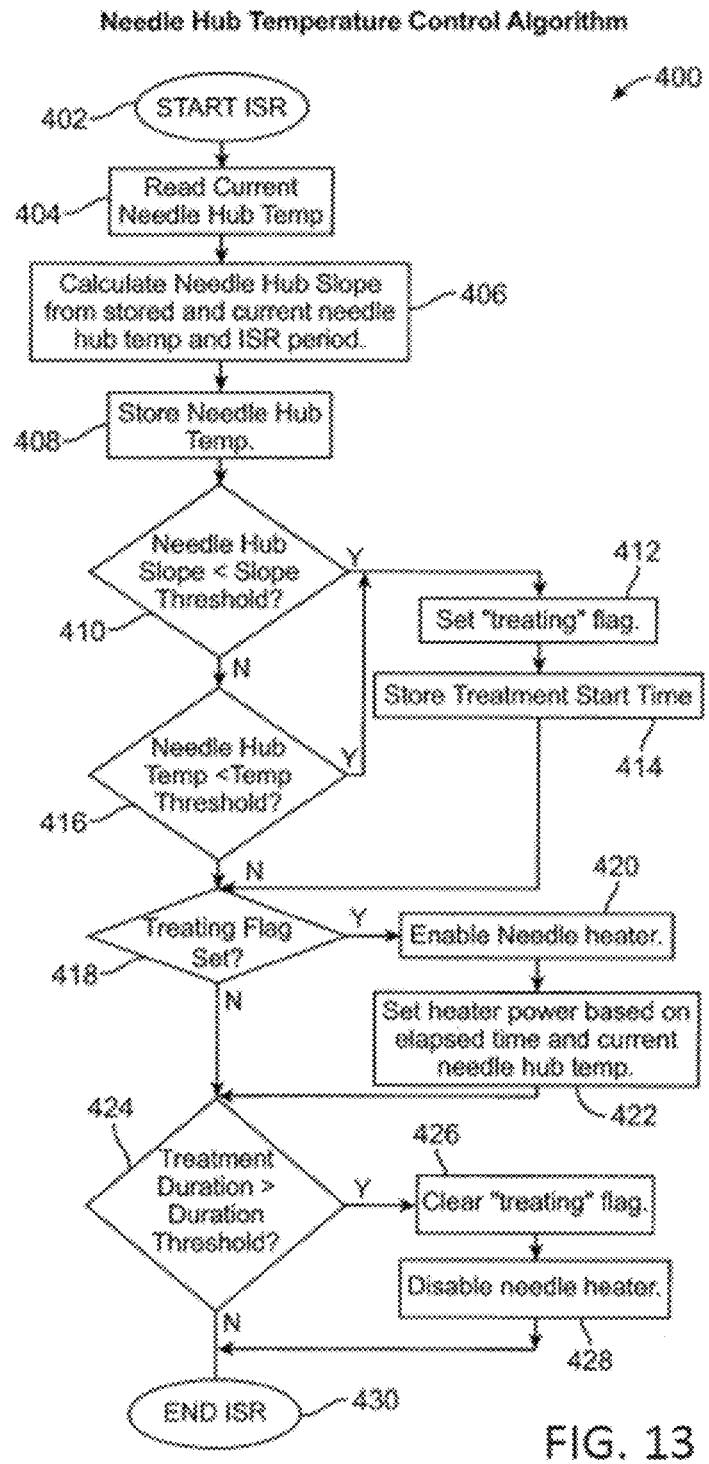
FIG. 13 is a flow chart illustrating an exemplary algorithm for heating the needle probe of FIG. 3A, according to some embodiments of the invention.

An exemplary algorithm 400 for controlling the heater element 314, and thus for transferring heat to the cladding 320, is illustrated in FIG. 13. In FIG. 13, the start of the interrupt service routine (ISR) 402 begins with reading the current needle hub temperature 404 using a temperature sensor such as a thermistor or thermocouple disposed near the needle hub. The time of the measurement is also recorded. This data is fed back to controller 22 where the slope of a line connecting two points is calculated. The first point in the line is defined by the current needle hub temperature and time of its measurement and the second point consists of a previous needle hub temperature measurement and its time of measurement. Once the slope of the needle hub temperature curve has been calculated 406, it is also stored 408 along with the time and temperature data. The needle hub temperature slope is then compared with a slope threshold value 410. If the needle hub temperature slope is less than the threshold value then a treating flag is activated 412 and the treatment start time is noted and stored 414. If the needle hub slope is greater than or equal to the slope threshold value 410, an optional secondary check 416 may be used to verify that cooling has not been initiated. In step 416, absolute needle hub temperature is compared to a temperature threshold. If the hub temperature is less than the temperature threshold, then the treating flag is activated 412 and the treatment start time is recorded 414 as previously described. As an alternative, the shape of the slope could be compared to a norm, and an error flag could be activated for an out of norm condition. Such a condition could indicate the system was not heating or cooling sufficiently. The error flag could trigger an automatic stop to the treatment with an error indicator light. Identifying the potential error condition and possibly stopping the treatment may prevent damage to the proximal tissue in the form of too much heat, or too much cooling to the tissue. The algorithm preferably uses the slope comparison as the trigger to activate the treatment flag because it is more sensitive to cooling conditions when the cryogenic device is being used rather than simply measuring absolute temperature. For example, a needle probe exposed to a cold environment would gradually cool the needle down and this could trigger the heater to turn on even though no cryogenic cooling treatment was being conducted. The slope more accurately captures rapid decreases in needle temperature as are typically seen during cryogenic treatments.

When the treatment flag is activated 418 the needle heater is enabled 420 and heater power may be adjusted based on the elapsed treatment time and current needle hub temperature 422. Thus, if more heat is required, power is increased and if less heat is required, power is decreased. Whether the treatment flag is activated or not, as an additional safety mechanism, treatment duration may be used to control the heater element 424. As mentioned above, eventually, cryogenic cooling of the needle will overcome the effects of the heater element. In that case, it would be desirable to discontinue the cooling treatment so that the proximal region of the probe does not become too cold and cause skin damage. Therefore, treatment duration is compared to a duration threshold value in step 424. If treatment duration exceeds the duration threshold then the treatment flag is cleared or deactivated 426 and the needle heater is deactivated 428. If the duration has not exceeded the duration threshold 424 then the interrupt service routine ends 430. The algorithm then begins again from the start step 402. This process continues as long as the cryogenic device is turned on.

Preferred ranges for the slope threshold value may range from about −5° C. per second to about −90° C. per second and more preferably range from about −30° C. per second to about −57° C. per second. Preferred ranges for the temperature threshold value may range from about 15° C. to about 0° C., and more preferably may range from about 0° C. to about 10° C. Treatment duration threshold may range from about 15 seconds to about 75 seconds.

It should be appreciated that the specific steps illustrated in FIG. 13 provide a particular method of heating a cryogenic probe, according to an embodiment of the present invention. Other sequences of steps may also be performed according to alternative embodiments. For example, alternative embodiments of the present invention may perform the steps outlined above in a different order. Moreover, the individual steps illustrated in FIG. 13 may include multiple sub-steps that may be performed in various sequences as appropriate to the individual step. Furthermore, additional steps may be added or removed depending on the particular applications.

Figure 14:
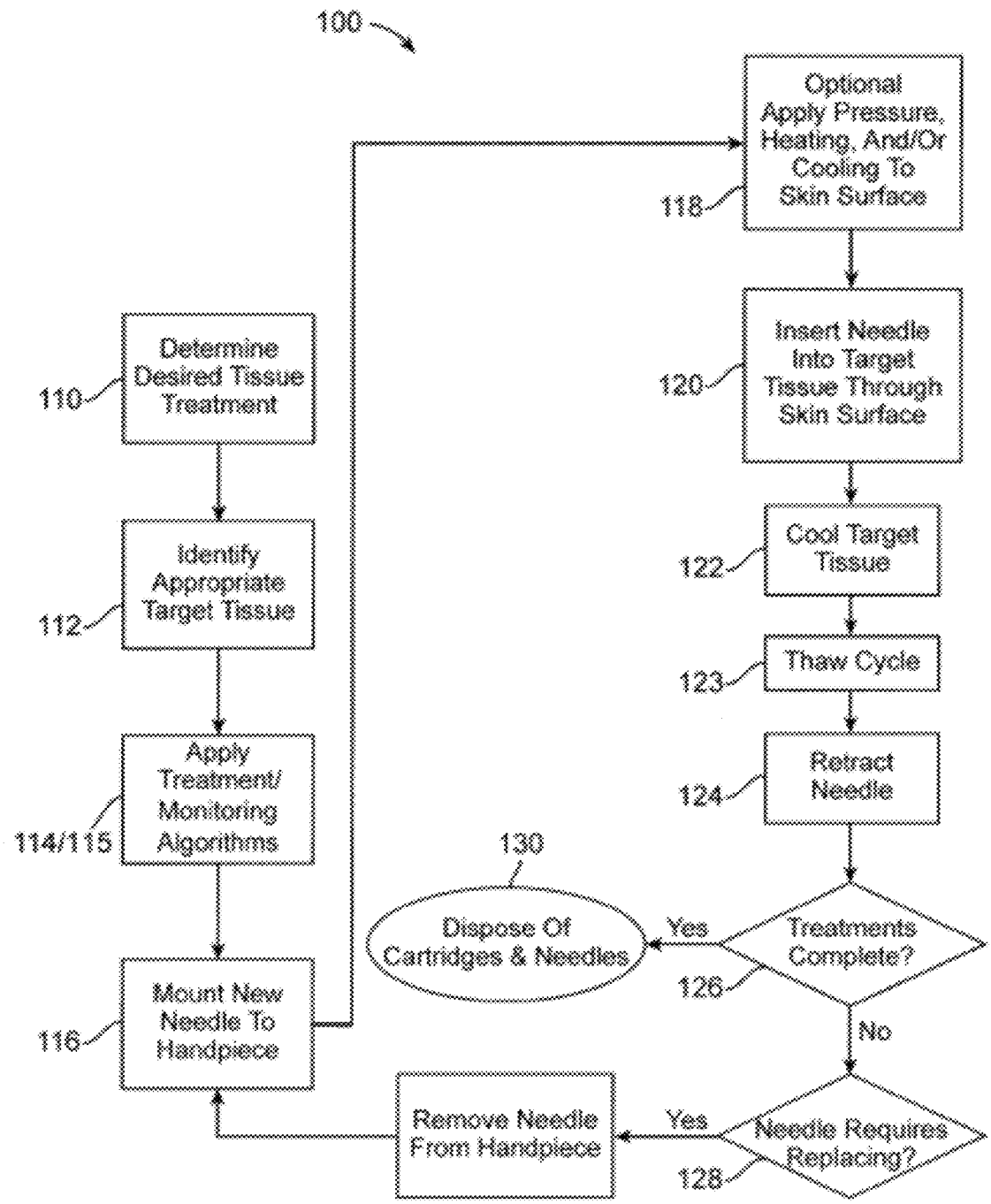
FIG. 14 is a flow chart schematically illustrating an exemplary method for treatment using the disposable cryogenic probe and system of FIGS. 1A and 1B, according to some embodiments of the invention.

The heating algorithm may be combined with a method for treating a patient. Referring now to FIG. 14, a method 100 facilitates treating a patient using a cryogenic cooling system having a reusable or disposable handpiece either of which that can be self-contained or externally powered with replaceable needles such as those of FIG. 1B and a limited capacity battery or metered electrical supply. Method 100 generally begins with a determination 110 of the desired tissue therapy and results, such as the inhibition of pain from a particular site. Appropriate target tissues for treatment are identified 112 (a tissue that transmits the pain signal), allowing a target treatment depth, target treatment temperature profile, or the like to be determined. Step 112 may include performing a tissue characterization and/or device diagnostic algorithm, based on power draw of system 10, for example.

The application of the treatment algorithm 114 may include the control of multiple parameters such as temperature, time, cycling, pulsing, and ramp rates for cooling or thawing of treatment areas. In parallel with the treatment algorithm 114, one or more power monitoring algorithms 115 can be implemented. An appropriate needle assembly can then be mounted 116 to the handpiece, with the needle assembly optionally having a needle length, skin surface cooling chamber, needle array, and/or other components suitable for treatment of the target tissues. Simpler systems may include only a single needle type, and/or a first needle assembly mounted to the handpiece.

Pressure, heating, cooling, or combinations thereof may be applied 118 to the skin surface adjacent the needle insertion site before, during, and/or after insertion 120 and cryogenic cooling 122 of the needle and associated target tissue. Non-target tissue directly above the target tissue can be protected by directly conducting energy in the form of heat to the cladding on a proximal portion of the needle shaft during cooling. Upon completion of the cryogenic cooling cycle the needles will need additional "thaw" time 123 to thaw from the internally created cooling zone to allow for safe removal of the probe without physical disruption of the target tissues, which may include, but not be limited to nerves, muscles, blood vessels, or connective tissues. This thaw time can either be timed with the refrigerant valve shut-off for as short a time as possible, preferably under 15 seconds, more preferably under 5 seconds, manually or programmed into the controller to automatically shut-off the valve and then pause for a chosen time interval until there is an audible or visual notification of treatment completion.

Heating of the needle may be used to prevent unwanted skin damage using the apparatus and methods previously described. The needle can then be retracted 124 from the target tissue. If the treatment is not complete 126 and the needle is not yet dull 128, pressure and/or cooling can be applied to the next needle insertion location site 118, and the additional target tissue treated. However, as small gauge needles may dull after being inserted only a few times into the skin, any needles that are dulled (or otherwise determined to be sufficiently used to warrant replacement, regardless of whether it is after a single insertion, 5 insertions, or the like) during the treatment may be replaced with a new needle 116 before the next application of pressure/cooling 118, needle insertion 120, and/or the like. Once the target tissues have been completely treated, or once the cooling supply canister included in the self-contained handpiece is depleted, the used canister and/or needles can be disposed of 130. The handpiece may optionally be discarded.

Figure 15A:
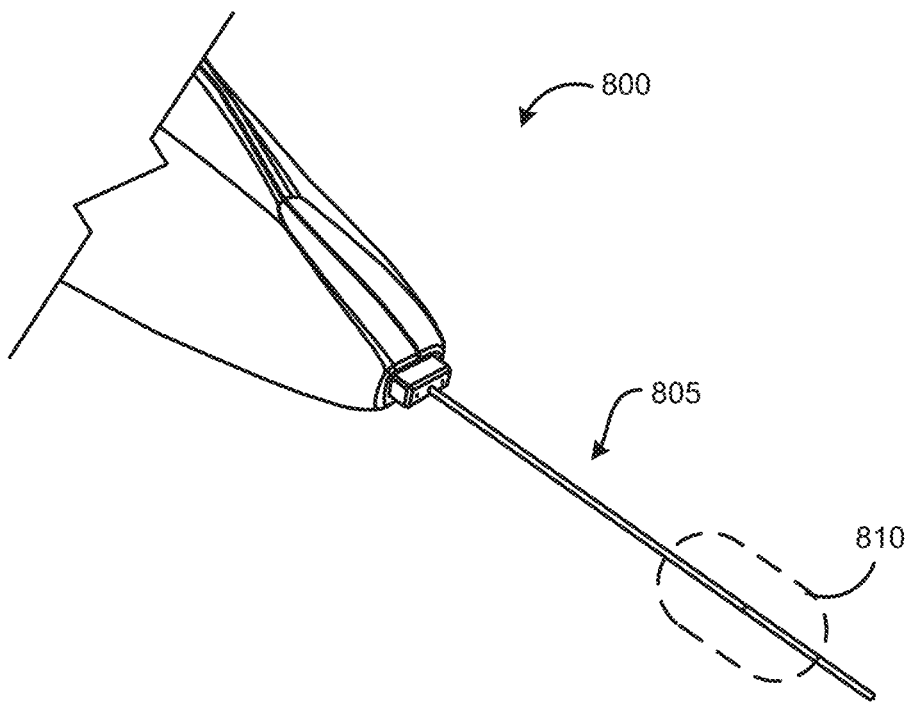
FIGS. 15A and 15B illustrate an exemplary system according to some embodiments.
Figure 15B:
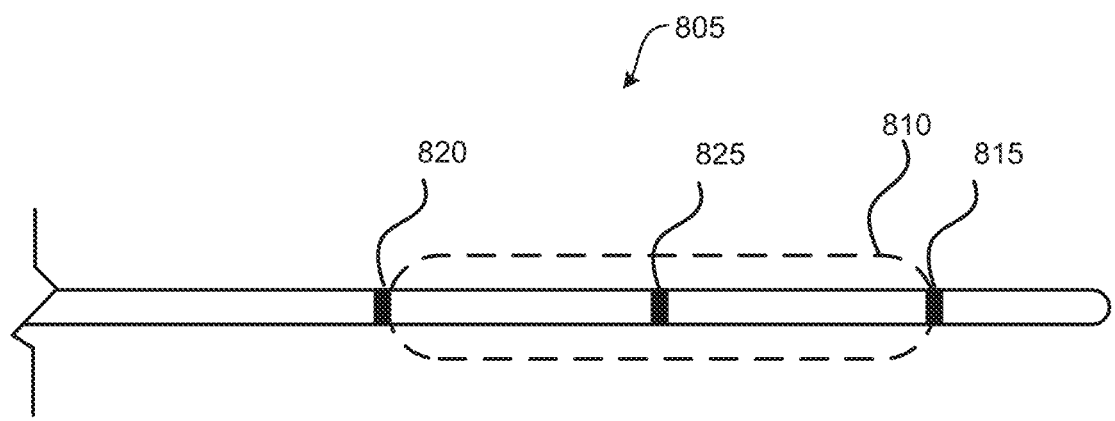

FIGS. 15A-15B illustrate a distal end of an exemplary cryoprobe 800 for treating a nerve according to some embodiments. The probe 800 may have a needle 805 extending distally that is configured to generate a cryozone 810. In some embodiments, as illustrated in the close up of needle 805 in FIG. 15B, the needle 805 may include one or more marks along the length of the needle. The one or more marks may comprise a mark 815 for marking a distal end of the cryozone 810 that is generated by the probe 800, a mark 820 for marking a proximal end of the cryozone 810 that is generated by the probe 800, and/or a mark 825 for marking a center of a the cryozone 810 that is generated by the probe 800.

Figure 16:
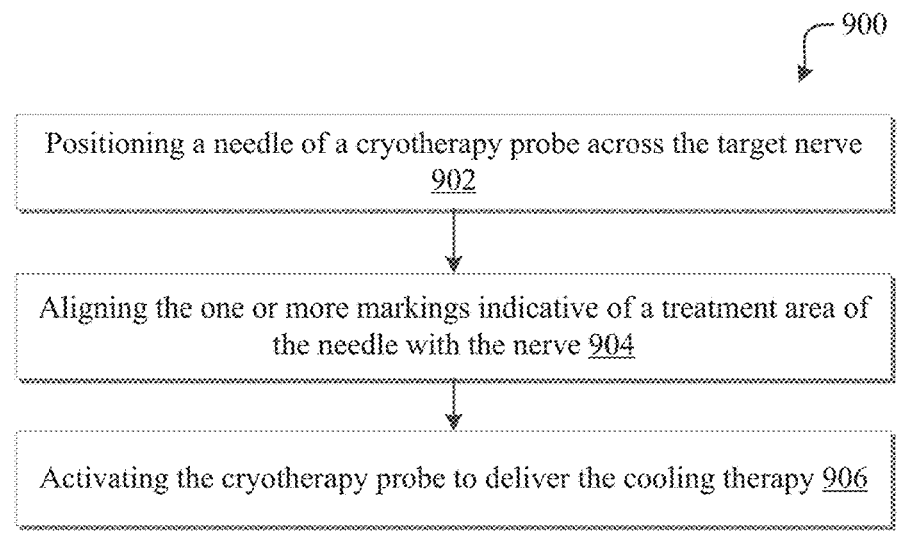
FIG. 16 illustrates an exemplary method of treating a nerve according to some embodiments.

The marks 815, 820, 825 may be utilized for visually aligning the needle 805 of a probe 800 with a target nerve. For example, FIG. 16 illustrates an exemplary method 900 of treating a nerve according to some embodiments. At step 902, a needle of the cryotherapy probe is positioned across the target nerve. The one or more markings indicative of a treatment area (e.g., marks 815, 820, 825) of the needle may be aligned with the nerve 904. After alignment, the cryotherapy probe may be activated to deliver the cooling therapy 906.

In some embodiments, the needle may be provided with an echogenic coating that makes the needle more visible under ultrasound imaging. For example, in some embodiments, the entire length of the needle may be provided with an echogenic coating. Alternatively, the one or more of the marks 815, 820, 825, may be provided with an echogenic coating such that the distal end, proximal end, or center of the cryozone associated with the needle is visible under ultrasound imaging. In other embodiments, the one or more marks may be provided by a lack of echogenic coating. For example, in some embodiments, the length of the needle may be provided with an echogenic coating except for at the one or more marks 815, 820, 825, such that when viewed under ultrasound guidance, the distal, proximal, or center of the cryozone would be associated with the portion of the needle without the echogenic coating. Alternatively, the length of the needle may be provided with the echogenic coating that ceases at the center of the associated cryozone, such that when viewed under ultrasound guidance, the distal end of the echogenic coating would be associated with a center of a cryozone of the needle.

Long needles may be used in some embodiments (e.g., 8-15 mm, 20 mm, 90 mm etc.). Longer needles may require a smaller gauge (larger diameter) needle so they have sufficient rigidity to maintain consistent spacing when placed deep in the tissue, but not so large as to create significant mechanical injury to the skin and tissue when inserted (e.g., greater than 20 ga). Alternate configurations of the device may have two or more needles spaced generally 3-5 mm apart of lengths ranging from up to 20 mm or greater, typically of 25 gauge or 23 gauge. Single needle configurations may be even longer (e.g., 90 mm) for reaching target tissues that are even deeper (e.g., >15 mm or so below the dermis). Longer needle devices (e.g., >10 mm) may not need active heating of the skin warmer and/or cladding found in designs using shorter needle(s) as the cooling zone may be placed sufficiently deep below the dermis to prevent injury. In some embodiments, devices with single long needle configurations may benefit from active nerve location such as ultrasound or electrical nerve stimulation to guide placement of the needle. Further, larger targets may require treatment from both sides to make sure that the cold zone created by the needle fully covers the target. Adjacent treatments placing the needle to either side of a nerve during two successive treatment cycles may still provide an effective treatment of the entire nerve cross-section.

In some situations, a probe with multiple spaced apart needles may be preferable (e.g., 2, 3, 4 or more). A device employing multiple needles may decrease the total treatment duration by creating larger cooling zones. Further, a multi-needle device may be configured to provide continuous cooling zones between the spaced apart needles. In some embodiments, the needles may be spaced apart by 1-5 mm. The spacing may be dependent on the type of tissue being targeted. For example, when targeting a nerve, it may be preferable to position the nerve between the two or more needles so that cooling zones are generated on both sides of the nerve. Treating the nerve from both sides may increase the probability that the entire cross-section of the nerve will be treated. For superficial peripheral nerves, the nerves may be at depths ranging from 2-6 mm and may be smaller in diameter, typically <2 mm. Accordingly, devices for treating superficial peripheral nerves may comprises two or more 27 gauge needles spaced ≤2 mm apart and having typical lengths less than 7 mm (e.g., 6.9 mm); however longer needles may be required to treat the full patient population in order to access patients with altered nerve anatomy or patients with higher amounts of subcutaneous tissue such as those with high BMIs.

A treatment cycle may comprise a 10 second pre-warm phase, followed by a 60 second cooling phase, followed thereafter by a 15 second post-warm phase with 40° C. skin warmer throughout. It should be understood that other treatment cycles may be implemented. In some embodiments, a pre-warming cycle can range from 0 to up to 30 seconds, preferably 5-15 seconds sufficient to pre-warm the cryoprobe and opposing skin. Treatment cooling may range from 5-120 seconds, preferably 15-60 seconds based on the flow rate, geometry of the cryoprobe, size of the therapy zone, size of the target nerve or tissue and the mechanism of action desired. Post-warming can range from 0-60 seconds, preferably 10-15 seconds sufficient to return the cryoprobe to a steady state thermal condition and possibly to free the cryoprobe needle(s) from the frozen therapy zone (e.g., at least 0° C.) prior to removing the cryoprobe needles. For example, in some embodiments, devices with 6.9 mm long cladded needles may be warmed with a 30° C. heater. The treatment cycle may comprise a 10 second pre-warm phase, a 35 second cooling phase, and a 15 second post-warm phase. Advantageously, such a treatment cycle may make an equivalent cryozone as the treatment cycle used in the study in a shorter amount of time (e.g., a 35 second cooling phase compared to a 60 second cooling phase).

In some embodiments, treatment devices and treatment cycles may be configured to deliver a preferred cryozone volume. For example, in some embodiments, devices and treatment cycles may be configured to generate cryozones (defined by the 0° C. isotherm) having a cross-sectional area of approximately 14-55 mm2 (e.g., 27 mm2). Optionally, the devices and treatment cycles may be configured to generate cryozones having a volume of approximately 65-125 mm3 (e.g., 85 mm3).

Accordingly, in some embodiments, treatment cycles may be configured with cooling phases ranging between 15-75 seconds (e.g., 30 seconds, 35 seconds, 40 seconds, 45 seconds, etc.) depending on cooling fluid flow rates, warming phase durations, warming phase temperature, number of cooling needles, needle spacing, or the like in order to generate a desired cryozone. Similarly, treatment cycles may be configured with warming phases operating a temperature ranging between 10-45° C. depending on the length of cooling phases, number of needles, needle spacing, etc. in order to generate a desired cryozone. Generally, with higher degree warming phases, the duration of the pre-warm phase and the cooling phase will be longer, however the post-warm phase duration may be reduced. In some embodiments the temperature can be set to one temperature during the pre-warm phase, another temperature during the cooling phase, and a third temperature during the post-warm phase.

In some embodiments, devices may be configured to limit flow rate of a cooling fluid to approximately 0.34-0.80 SLPM (gas phase). Optionally, in some embodiments, it may be preferable to configure the device and the treatment cycle to maintain the tip a less than −55° C. during cooling phases. In some embodiments, it may be preferable to configure the device and the treatment cycle to have the tip return to at least 0° C. at the end of the post-warm phase so as to ensure the device may be safely removed from the tissue after the treatment cycle.

While generally describing treatment cycles as including pre-heating/warming phases, it should be understood that other treatment cycles may not require a pre-heating/warming phase. For example, larger needle devices (e.g., 30-90 mm) may not require a pre-heat/warm phase. Larger needles may rely on the body's natural heat to bring the needle to a desired temperature prior to a cooling phase.

In some embodiments of the present invention, treatment guidance can rely on rigid or boney landmarks because they are less dependent upon natural variations in body size or type, e.g., BMI. Soft tissues, vasculature and peripheral nerves pass adjacent to the rigid landmarks because they require protection and support. The target nerve to relieve pain can be identified based on the diagnosis along with patients identifying the area of pain, biomechanical movements that evoke pain from specific areas, palpation, and diagnostic nerve blocks using a temporary analgesic (e.g., 1-2% Lidocaine). Target nerve (tissue) can be located by relying on anatomical landmarks to indicate the anatomical area through which the target nerve (tissue) reside. Alternatively, nerve or tissue locating technologies can be used. In the case of peripheral nerves, electrical stimulation or ultrasound can be used to locate target nerves for treatment. Electrical nerve stimulation can identify the nerve upon stimulation and either innervated muscle twitch in the case of a motor nerve or altered sensation in a specific area in the case of a sensory nerve. Ultrasound is used to visualize the nerve and structures closely associated with the nerve (e.g., vessels) to assist in placing the cryoprobe in close proximity to the target nerve. By positioning the patient's skeletal structure in a predetermined position (e.g., knee bent 30 degrees or fully extended), one can reliably position the bones, ligaments, cartilage, muscle, soft tissues (including fascia), vasculature, and peripheral nerves. External palpation can then be used to locate the skeletal structure and thereby locate the pathway and relative depth of a peripheral nerve targeted for treatment.

A treatment of peripheral nerve tissue to at least −20° C. for greater than 10 seconds (e.g., at least 20 seconds preferably) may be sufficient to trigger 2nd degree Wallerian degeneration of the axon and myelinated sheath. Conduction along the nerve fibers is stopped immediately following treatment. This provides immediate feedback as to the location of the target peripheral nerve or associated branches when the associated motion or sensation is modified. This can be used to refine rigid landmark guidance of future treatments or to determine whether addition treatment is warranted.

By using rigid landmarks, one may be able to direct the treatment pattern to specific anatomical sites where the peripheral nerve is located with the highest likelihood. Feedback from the patient immediately after each treatment may verify the location of the target peripheral nerve and its associated branches. Thus, it should be understood that in some embodiments, the use of an electrical nerve stimulation device to discover nerve location is not needed or used, since well-developed treatment zones can locate target nerves. This may be advantageous, due the cost and complexity of electrical nerve stimulation devices, which are also not always readily available.

In alternative embodiments of the invention, one could use an electrical nerve stimulation device (either transcutaneous or percutaneous) to stimulate the target peripheral nerve and its branches. With transcutaneous electrical nerve stimulation (TENS) the pathway of the nerve branch can be mapped in XY-coordinates coincident with the skin surface. The Z-coordinate corresponding to depth normal to the skin surface can be inferred by the sensitivity setting of the electrical stimulation unit. For example, a setting of 3.25 mA and pulse duration of 0.1 ms may reliably stimulate the frontal branch of the temporal nerve when it is within 7 mm of the skin surface. If a higher current setting or longer pulse duration is required to stimulate the nerve, then the depth may be >7 mm. A percutaneous electrical nerve stimulator (PENS) can also be used to locate a target peripheral nerve. Based on rigid anatomical landmarks, a PENS needle can be introduced through the dermis and advanced into the soft tissues. Periodic stimulating pulses at a rate of 1-3 Hz may be used to stimulate nerves within a known distance from the PENS needle. When the target nerve is stimulated, the sensitivity of the PENS can be reduced (e.g., lowering the current setting or pulse duration) narrowing the range of stimulation. When the nerve is stimulated again, now within a smaller distance, the PENS sensitivity can be reduced further until the nerve stimulation distance is within the therapy zone dimensions. At this point, the PENS needle can be replaced with the focused cold therapy needle(s) and a treatment can be delivered. The PENS and focused cold therapy needles can be introduced by themselves or through a second larger gage needle or cannula. This may provide a rigid and reproducible path when introducing a needle and when replacing one needle instrument with another. A rigid pathway may guide the needle to the same location by preventing needle tip deflection, which could lead to a misplaced therapy and lack of efficacy.

While many of the examples disclosed herein related to puncturing the skin in a transverse manner to arrive at a target nerve, other techniques can be used to guide a device to a target nerve. For example, insertion of devices can be made parallel to the surface of the skin, such that the (blunted) tip of the device glides along a particular fascia to arrive at a target sensory nerve. Such techniques and devices are disclosed in U.S. Pub. No. 2012/0089211, the entirety of which is incorporated by reference. Possible advantages may include a single insertion site, and guidance of a blunt tip along a layer common with the path or depth of the target nerve. This technique may be a position-treatment-thaw, reposition-treatment-thaw, etc.

In further aspects of the present invention, a focused cold therapy treatment device may be provided that is adapted to couple with or be fully integrated with a nerve stimulation device such that nerve stimulation and focused cold therapy may be performed concurrently with the cryo-stimulation device. Accordingly, embodiments of the present disclosure may improve nerve targeting during FCT procedures. Improvements in nerve localization and targeting may increase treatment accuracy and physician confidence in needle placement during treatment. In turn, such improvements may decrease overall treatment times, the number of repeat treatments, and the re-treatment rate. Further, additional improvements in nerve localization and targeting may reduce the number of applied treatment cycles and may also reduce the number of cartridge changes (when replaceable refrigerant cartridges are used). Thus, embodiments of the present disclosure may provide one or more advantages for FCT by improving localization and treatment of target nerves. Hence, some aspects of the present disclosure provide methods, devices, and systems for localizing and targeting a nerve with focused cold therapy.

Figure 17:
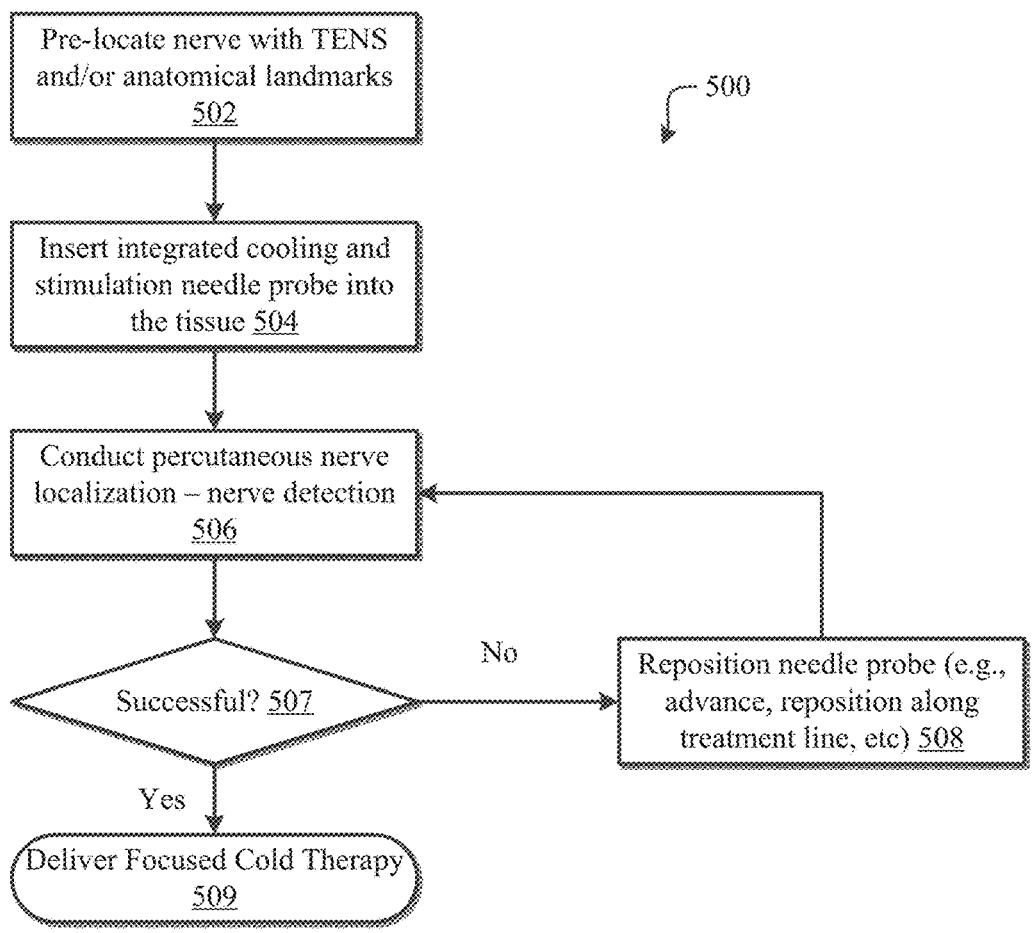
FIG. 17 illustrates another exemplary method of locating and treating a nerve according to some embodiments.

FIG. 17 illustrates one such method 500 of locating and treating a nerve according to some embodiments. At step 502, a transcutaneous electrical stimulation (TENS) device and/or anatomical landmarks may be used to pre-locate a target nerve or otherwise generally locate a target nerve location. At step 504, one or more needles of an integrated cooling and stimulation device may be inserted into the tissue. At step 506, percutaneous nerve localization may be conducted to determine 507 whether the one or more needles is proximal to the target nerve. If the nerve localization using percutaneous nerve stimulation 506 is unsuccessful, the one or more needles may be repositioned 508 within the tissue. Thereafter, percutaneous nerve localization 506 may be conducted again to determine whether the repositioning successfully places the one or more needles sufficiently proximal to the target nerve. If the nerve localization using percutaneous nerve stimulation is successful upon insertion 504 or after repositioning 508, the focused cold therapy may then be delivered 509 using one or more needles of the treatment device.

The method 500 may be used for cosmetic and/or other medical treatments (e.g., pain alleviation or the like). In some cosmetic applications, a target nerve may be between 3-7 mm in depth, for example. In other medical applications, a target nerve may be upwards of 50 mm in depth or deeper. It may be beneficial to locate the target nerve to within 2 mm for at least some of treatments. Additionally, in some applications, it may be beneficial to be able to locate and differentiate motor nerves from sensory nerves. For example, in some cosmetic applications that target motor nerves for wrinkle alleviation, it may be advantageous to locate and avoid treating sensory nerves to limit side effects due to the cosmetic procedure. For example, method 500 may be used to target the temporal branch of the facial nerve (TBFN). The nerve may run along the Pitanguy line at a depth of 0.5 mm above the SDTF layer. The depth of the SDTF layer varies along treatment lines and among individuals and as such the target nerve depth may also vary from patient to patient. Accordingly, an integrated stimulation and cooling treatment device may be beneficial in such a procedure. In an additional non-limiting example, method 500 may be used to target the infrapatellar branch of the saphenous nerve (ISN). The ISN is a sensory nerve that innervates the anterior aspect of the knee. Focused Cold Therapy of the ISN may alleviate pain experienced in the knee of a patient (e.g., due to osteoarthritis or the like). While anatomical features may be used to generally localize a treatment box for the target nerve, a plurality of treatments may be needed before the target nerve is treated within the box. Accordingly, an integrated nerve stimulation and cooling treatment device may provide more accurate treatments and may thereby limit the number of treatments required for treatment and reduce a treatment time. Additional treatments that may benefit from such a device include, but are not limited to: head pain, knee pain, plantar fasciitis, back pain, tendonitis, shoulder pain, movement disorders, intercostal pain, post-herpetic neuralgia, post-surgical pain, phantom limb pain, etc.

Electrical nerve stimulation localizes nerves by transmission of electrical pulses. The electrical impulses in turn excite nerves by inducing a flow of ions through the neuronal cell membrane (depolarization), which results in an action potential that may propagate bi-directionally. The nerve membrane depolarization may result in either muscle contraction or paresthesia, depending on the type of nerve fiber (motor vs. sensory). The current density a nerve reacts to or "sees" decreases with distance from the nerve:

$$I = k\left(\frac{i}{r^2}\right)$$

where k is a constant that depends on electrode size, pulse width, tissue impedance, nerve fiber size, etc.; i is the current delivered; and r is the distance from the nerve. This corresponds to higher threshold currents at a distance from the nerve.

In some embodiments, an insulated needle having a small conducting or uninsulated portion may have minimal current threshold when the needle is on the nerve. Non-insulated needles in contrast may transmit current through the entire length and may have a lower current density along the treatment portion of the needle. As such, non-insulated needles may require more current than insulated needles at the same distance from the nerve and may have less discrimination of distances as the needle approaches the nerve. Accordingly, while not essential, in some embodiments, cryo-stimulation devices may be provided that include an insulated nerve stimulation needle.

Figure 18A:
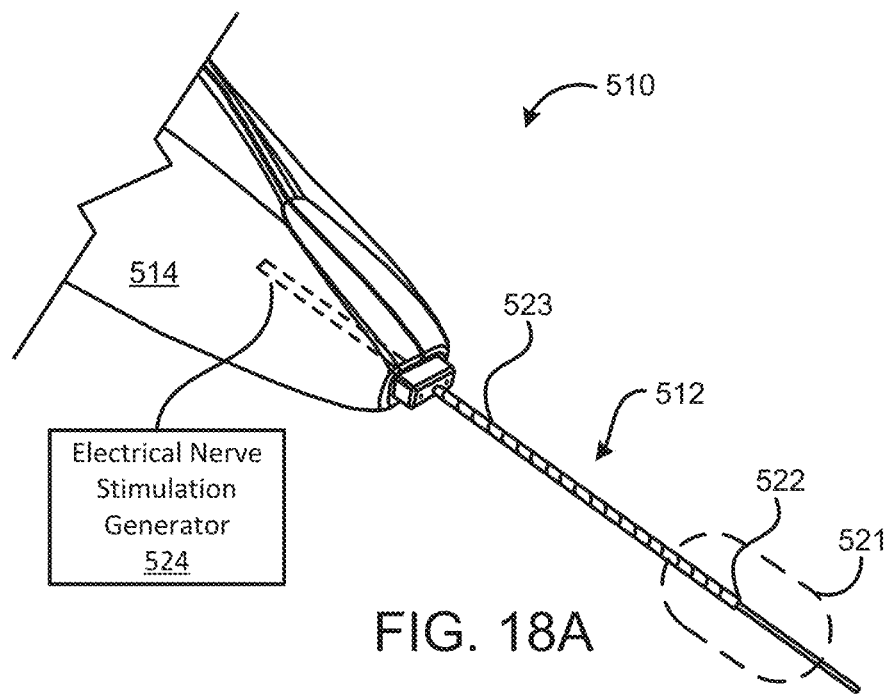
FIG. 18A illustrates an exemplary needle assembly according to some embodiments.
Figure 18B:
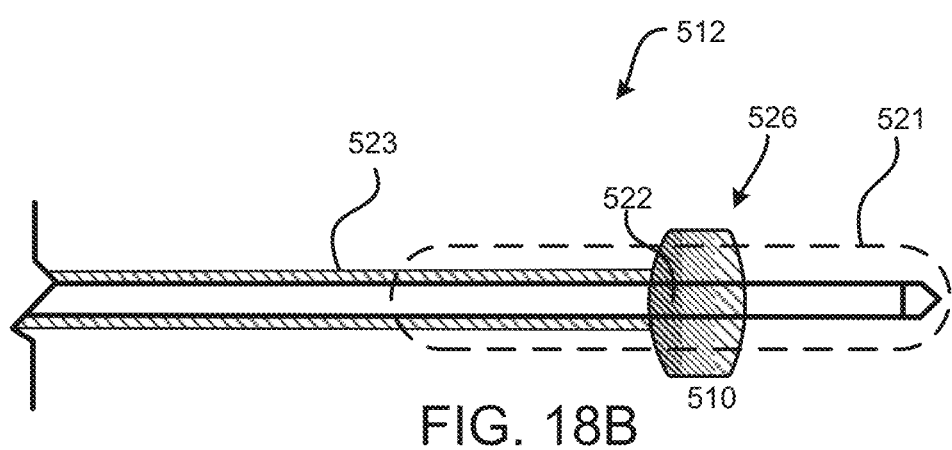
FIG. 18B illustrates a close up view of a needle of the exemplary needle assembly of FIG. 18A according to some embodiments.

In some embodiments, the integrated cooling and stimulation needle probe may have a single needle for both cooling and nerve stimulation. For example, FIG. 18A illustrates an exemplary needle assembly 510 having a single needle 512 that may be used to perform the method 500 according to some embodiments of the disclosure. FIG. 18B illustrates a close up view of the needle 512 of the exemplary needle assembly 510 of FIG. 18A according to some embodiments. In use, coolant may flow through the needle 512 (e.g. via cooling fluid supply tube or the like)

thereby cooling a distal end of the needle 512 and producing a cold zone 521 associated with the needle 512. The needle 512 may have a cooling center 522 along the length of the needle 512 that is associated with a center of the cold zone 521 produced by the needle 512. Additionally, the needle 512 may be constructed from an electrically conductive material and may also have an electrically insulated coating 523 disposed about a length of the needle 512. The electrically insulated coating 523 may electrically insulate a proximal portion of a length of the needle 512 that is adjacent the distal end of the housing 514 and may extend toward a distal portion of the length of the needle 512. The electrically insulated coating 523 may be a fluoropolymer coating, a silicone rubber coating, a parylene coating, a ceramic coating, an epoxy coating, a polyimide coating or the like. A proximal end of needle 512 may be uninsulated and may be configured to couple with an electrical nerve stimulation generator 524 of a percutaneous electrical stimulation device. A distal end of needle 512 may be uninsulated such that an electrical field 526 (FIG. 18B) generated by electrical nerve stimulation generator 524 happens about the distal end of needle 512. In some embodiments, the distal end of the electrically insulated coating 523 may be at the cooling center 522 of the needle 512. In such embodiments, the intensity of the electrical field 526 produced by electrical nerve stimulation generator 524 may be co-incident with the center of the cold zone 521 that is produced by the needle 512, as illustrated in FIG. 18B.

Figure 18C:
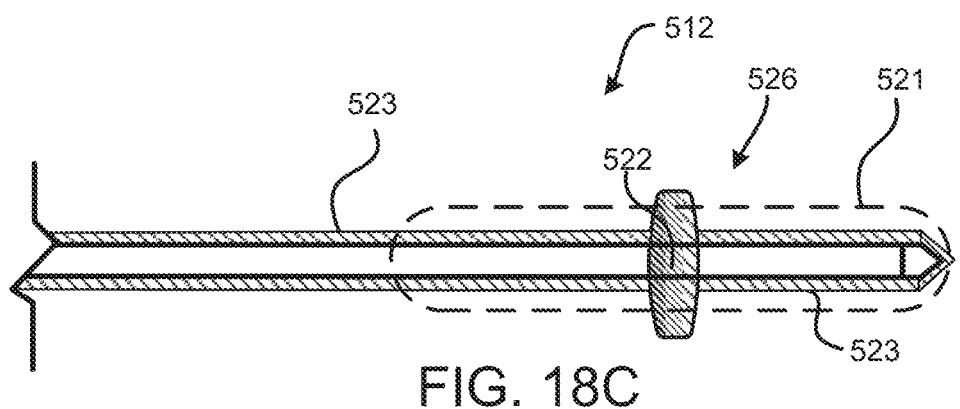
FIG. 18C illustrates an exemplary needle configuration according to some embodiments.

In some embodiments the coating 523 may be 0.00125 inches thick. Optionally, coating 523 may be applied by masking off the cooling center 522 of needle 512 and then coating the needle 512 with the electrically insulating material 523. Additionally, while needle assembly 510 is illustrated with a needle 512 without insulation at the distal end of the needle 512, it should be understood that this is exemplary. In some embodiments of the present disclosure, the distal end of needle 512 may have a coating of the electrically insulating material 523, as illustrated in FIG. 18C, while the portion of the needle 512 associated with the center of the cold zone 521 remains uninsulated.

Figure 19:
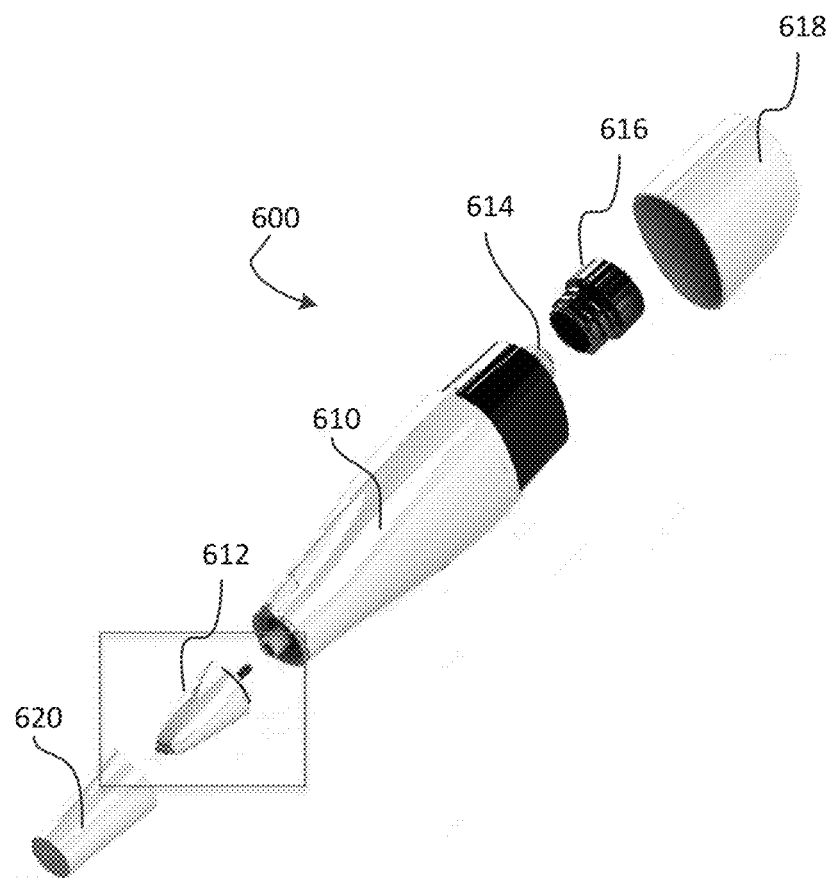
FIG. 19 illustrates an exemplary treatment system with a replaceable needle assembly having an electrical port for coupling with a waveform generator of a percutaneous electrical stimulation device according to some embodiments.

As mentioned above, a proximal end of needle 512 may be uninsulated and may be configured to couple with an electrical nerve stimulation generator 524. In some embodiments, the electrical nerve stimulation generator 524 may have an input that is configured to couple with a corresponding electrical port of the treatment device. For example, FIG. 19 illustrates an exemplary treatment device 600. The treatment device 600 includes a handle 610 that is configured to be coupled with a replaceable needle assembly 612. The handle 610 may further include a replaceable refrigerant cartridge 614. The cartridge 614 may be secured to handle 610 by a cartridge cap 616. The cartridge 614 and the cartridge cap 616 may be housed by distal cover 618. Optionally, a needle assembly cover 620 may be provided to house the needle assembly 612 when the device 600 is not in use.

Figure 20:
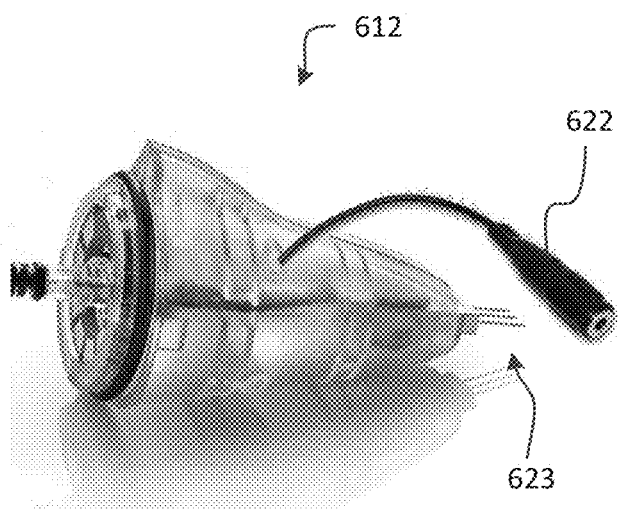
FIG. 20 illustrates the exemplary replaceable needle assembly of FIG. 19 according to some embodiments.

In some embodiments, the input electrical port configured to receive an input from the electrical nerve stimulation generator 524 may be provided on the replaceable needle assembly 612. For example, as illustrated in FIG. 20 illustrates an exemplary needle assembly 612 with an input electrical port 622. The input electrical port 622 is configured to couple with electrical nerve stimulation generator 524 to electrically couple the electrical nerve stimulation generator 524 with the uninsulated proximal portion of one or more electrical stimulation needles 623 of device 600.

Figure 21:
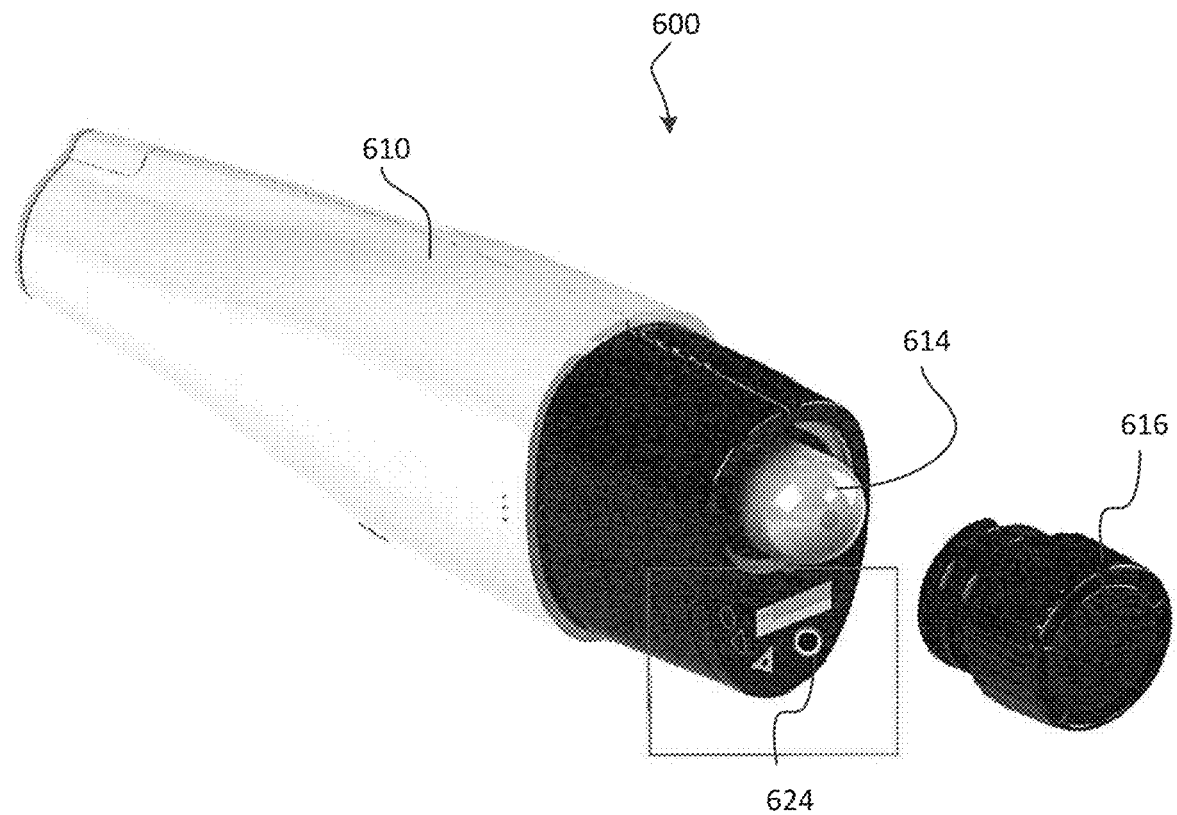
FIG. 21 illustrates yet another exemplary treatment system with a handle having an electrical port for coupling with a waveform generator of a percutaneous electrical nerve stimulation device according to some embodiments.
Figure 22:
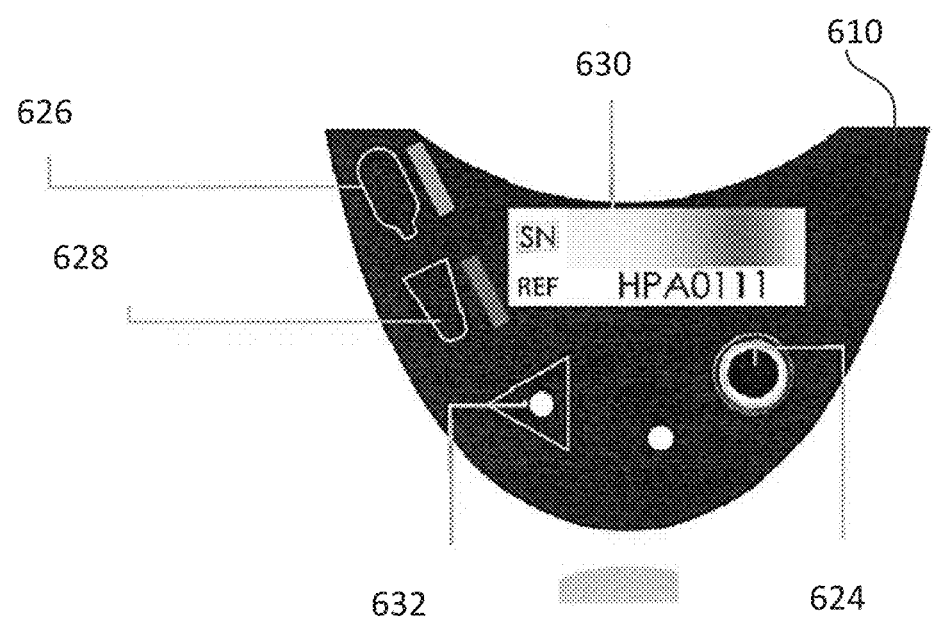
FIG. 22 illustrates a view of a proximal end of the exemplary treatment system of FIG. 21 according to some embodiments.

Additionally, in some embodiments, the input electrical port configured to receive an input from the electrical nerve stimulation generator 524 may be provided on the handle 610 in addition to or in the alternative to the electrical port 622 on needle assembly 612. For example, as illustrated in FIG. 21, a proximal end of handle 610 may include electrical port 624 for receiving an input from the electrical nerve stimulation generator 524. FIG. 22 illustrates a close up view of the proximal end of housing 610. As can be seen, the distal end of housing 610 may include a status light 626 for the cartridge status, a status light 628 for the needle assembly, a device serial number 630, and/or a reset access 632 in addition to electrical port 624. The one or more input electrical ports 622, 624 may be configured to be electrically coupled with one or more of the electrical stimulation needles of the device 600.

Figure 23:
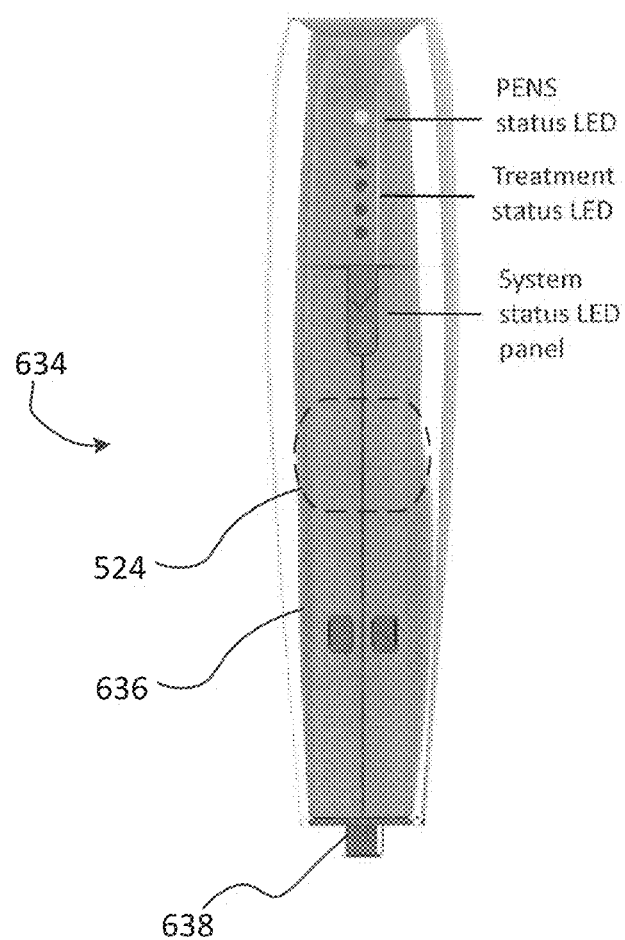
FIG. 23 illustrates yet another exemplary treatment system with a fully integrated percutaneous electrical stimulation device according to some embodiments.

Optionally, in some embodiments, the electrical nerve stimulation generator 524 may be fully integrated with the treatment device. For example, FIG. 23 illustrates yet another exemplary treatment system 634 with a fully integrated electrical nerve stimulation generator 524. The system 634 includes a housing 636 that defines a handle of the device. An electrical adapter 638 may be disposed at the distal end of housing 636 that is configured to electrically couple with a replaceable needle assembly (not shown). Housing 636 may house electrical nerve stimulation generator 524. Electrical nerve stimulation generator 524 may electrically couple with the adapter 638. Adapter 638 may provide an interface between the electrical nerve stimulation generator 524 and a replaceable needle assembly when the needle assembly is coupled with adapter 638.

Figure 24:
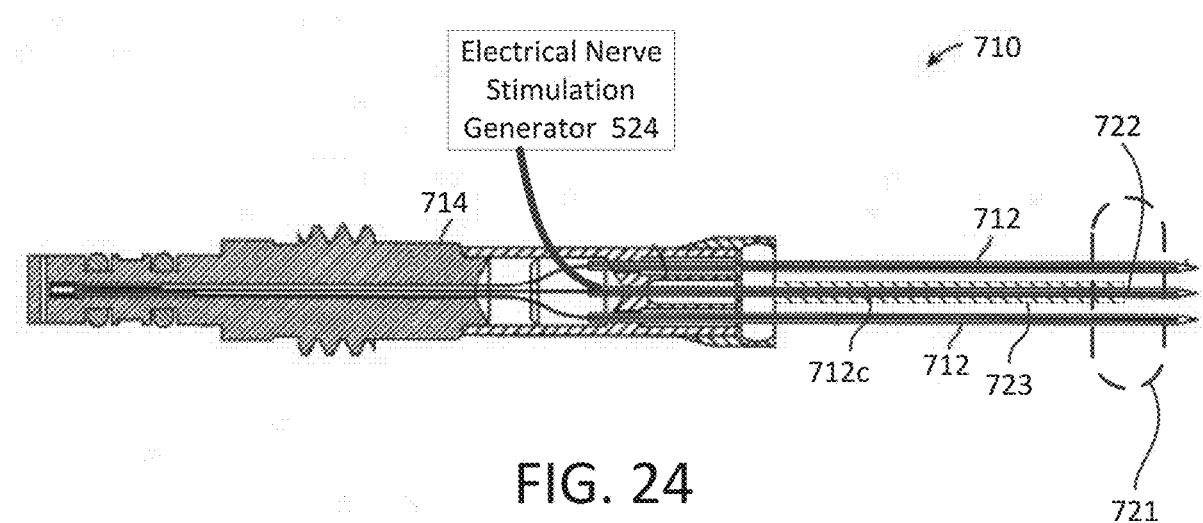
FIG. 24 illustrates another exemplary needle assembly according to some embodiments.

While the exemplary needle assembly 510 of FIG. 18A is illustrated with a single needle for performing the cooling treatment in addition to the nerve stimulation, it should be understood that other treatment devices or needle assemblies may be provided with a plurality of needles. One of skill in the art will appreciate that two, three, four, five, six, or more needles may be used. When a plurality of needles are used, they may be arranged in any number of patterns. For example, a single linear array may be used, or a two dimensional or three dimensional array may be used. Examples of two dimensional arrays include any number of rows and columns of needles (e.g. a rectangular array, a square array, elliptical, circular, triangular, etc.), and examples of three dimensional arrays include those where the needle tips are at different distances from the probe hub, such as in an inverted pyramid shape. Accordingly, in some embodiments, the integrated cooling and stimulation needle probe may have a plurality of needles for cooling and/or nerve stimulation. For example, FIG. 24 illustrates an exemplary needle assembly 710 that includes a plurality of needles 712 that may perform the method 500 with a plurality of needles according to some embodiments of the disclosure. In use, coolant may flow through one or more of the needles 712 thereby cooling a distal end of the one or more needles 712 and producing a cold zone 721 associated with the needle assembly 710. The needle assembly 710 may have a cooling center 722 that is associated with a center of the cold zone 721 produced by the one or more needles 712. Additionally, at least one of the needles 712 (in the illustrated embodiment, center needle 712c) may be constructed from an electrically conductive material and may also have an electrically insulated coating 723 disposed about a length of the needle 712c. The electrically insulated coating 723 may electrically insulate a proximal portion of a length of the needle 712c that is adjacent the distal end of the housing 714 and may extend toward a distal portion of the length of the needle 712c. The electrically insulated coating 723 may be a fluoropolymer coating, a silicone rubber coating, a parylene coating, a ceramic coating, an epoxy coating, a polyimide coating or the like. A proximal end of needle 712c may be uninsulated and may be configured to couple with the electrical nerve stimulation generator 524 of a percutaneous electrical stimulation device, e.g., through a manner described above, such as an electrical port on the needle assembly housing, an electrical port on the treatment device housing, an integrated generator 524 that electrically couples to needle 712c via an adapter between the device handle and the needle assembly 710 or the like. The portion of needle 712c that is disposed at the cooling center 722 may be uninsulated such that the intensity of the electrical field produced by electrical nerve stimulation generator 524 via needle 712c may be co-incident with the center of the cold zone 721 that is produced by the needle assembly 710.

While illustrated as including three needles 712, it should be understood that this is exemplary and non-limiting. Two, four, five or more needles may be provided in other embodiments. Further, while illustrated with each of the needles 712 being supplied by a cooling fluid supply tube and thus each of the needles 712 being configured to cool to produce cold zone 721, in other embodiments, only some of the plurality of needles may be configured to provide the cooling treatment. Other needles 712 may be provided separately for electrical stimulation. Accordingly, in some embodiments, center needle 712 may be provided for electrical stimulation only, while the adjacent needles 712 may be provided to produce cold zone 721. Put in another way, in some embodiments, stimulation needle (e.g., needle 712c) may not include a cold center along the length of the needle, but nevertheless, the cooling center 722 of the cold zone 721 associated with the needle assembly 710 may be disposed along the length of the stimulation needle. Thus, the stimulation needle may provide more accurate targeting of a target nerve with the cold zone 721 whether or not it provides cooling itself.

Additionally, it should be understood that while assembly 710 is illustrated with a single stimulating needle 712c, additional needles 712 of assembly 710 may be configured to separately stimulate as desired. Accordingly, some or all of the plurality of needles 712 may be configured to provide nerve stimulation. Thus, nerve stimulation generator 524 may be electrically coupled with each stimulating needle.

Further, in some embodiments, an adjacent needle (e.g., needles 712 adjacent to 712c) may provide an electrical ground during nerve stimulation. Accordingly, one or more of the adjacent needles may be constructed from a conductive material and may be uninsulated at a location proximate to an uninsulated portion of an adjacent nerve stimulation needle. Optionally, adjacent needles may also include an electrically insulated coating that extends from a proximal portion of the needle adjacent to the housing toward a distal portion of the needle.

In still further embodiments, during focused cold therapy delivery 509, nerve stimulation may be conducted to provide feedback to the treatment. For example, in some embodiments, nerve stimulation may be performed continuously concurrently with the focused cold therapy delivery 509 to determine the efficacy of the treatment in real time. Optionally, the nerve stimulation may be repeated in a discrete intervals during focused cold therapy delivery 509. In such embodiments, the focused cold therapy delivery 509 may continue until there is a cessation of motor function or paresthesia. In some embodiments, the focused cold therapy 509 may be shorter in duration when the nerve stimulation feedback is associated with a successful treatment. In other embodiments, the focused cold therapy 509 may be longer in duration when the nerve stimulation feedback indicates that the nerve has not been successfully treated. Further, initial tests surprisingly suggest that ice ball formation by the treatment needles of the assembly may be produced at a quicker rate when the electrical stimulation is concurrently delivered.

Figure 25:
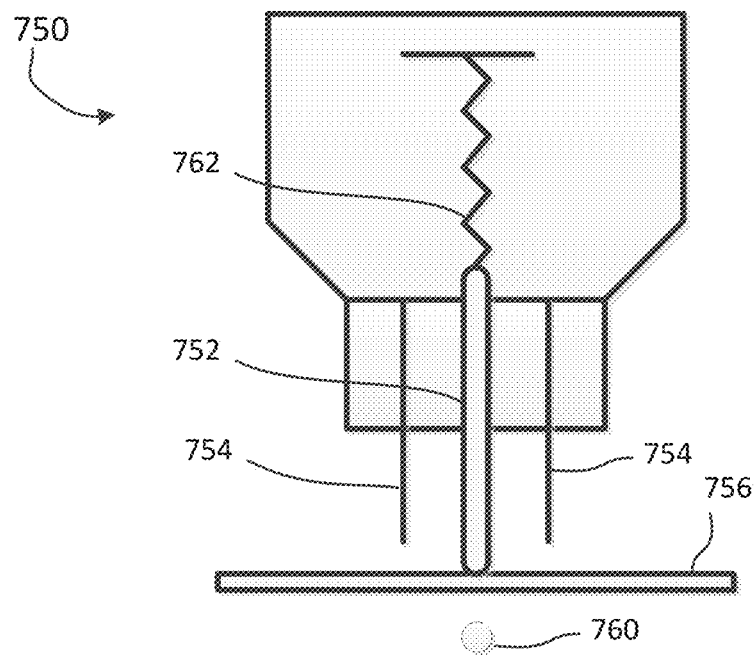
FIG. 25 illustrates an exemplary treatment system with an integrated transcutaneous electrical nerve stimulation probe according to some embodiments.
Figure 26:
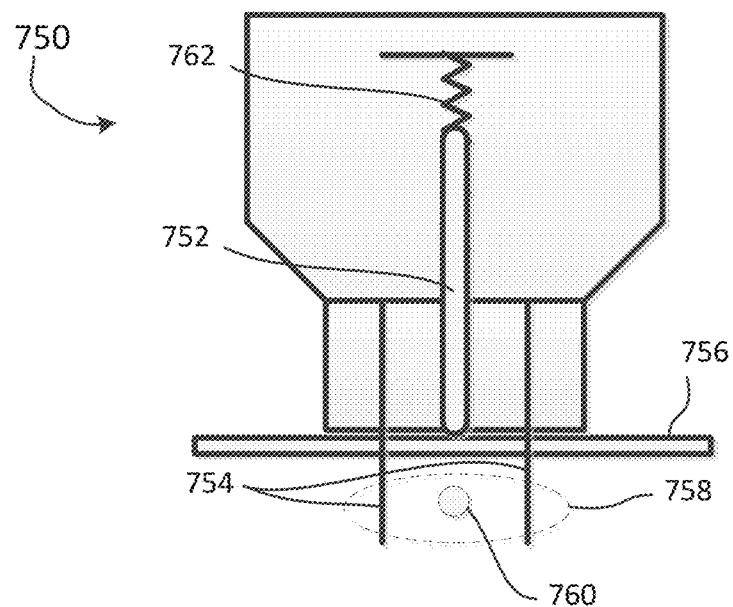
FIG. 26 illustrates an exemplary operation of the exemplary system of FIG. 24 according to some embodiments.

In still further embodiments of the present disclosure, a focused cold therapy treatment device may be provided with an integrated transcutaneous electrical stimulation device. For example, FIG. 25 illustrates an exemplary treatment system 750 with an integrated transcutaneous electrical stimulation probe 752 according to some embodiments. FIG. 26 illustrates an exemplary operation of the system 750 of FIG. 25 according to some embodiments. Treatment system 750 further includes two cooling treatment needles 754 for insertion through the tissue surface 756 to produce a cooling zone 758 to treat target nerve 760. The transcutaneous electrical stimulation probe 752 may have distal end for providing electrical stimulation through the tissue surface 756 for localizing the target nerve 760. A proximal portion of probe 752 may be coupled with a spring 762. After identifying a location of the target nerve 760, the device 750 may be pressed distally against the tissue surface 756 to insert needles 754 into the tissue. During needle 754 insertion, the spring 762 may compress and the probe 752 may withdraw into the housing of treatment system 750. Thereafter, the needles 754 may deliver the focused cold therapy to produce cold zone 758. Such an embodiment may localize a target nerve transcutaneously and may allow the treatment needles to be inserted into the tissue without having to first interchange the transcutaneous electrical stimulation device for the device with the cooling treatment needles.

One or more computing devices may be adapted to provide desired functionality by accessing software instructions rendered in a computer-readable form. When software is used, any suitable programming, scripting, or other type of language or combinations of languages may be used to implement the teachings contained herein. However, software need not be used exclusively, or at all. For example, some embodiments of the methods and systems set forth herein may also be implemented by hard-wired logic or other circuitry, including but not limited to application-specific circuits. Combinations of computer-executed software and hard-wired logic or other circuitry may be suitable as well.

Embodiments of the methods disclosed herein may be executed by one or more suitable computing devices. Such system(s) may comprise one or more computing devices adapted to perform one or more embodiments of the methods disclosed herein. As noted above, such devices may access one or more computer-readable media that embody computer-readable instructions which, when executed by at least one computer, cause the at least one computer to implement one or more embodiments of the methods of the present subject matter. Additionally or alternatively, the computing device(s) may comprise circuitry that renders the device(s) operative to implement one or more of the methods of the present subject matter.

Any suitable computer-readable medium or media may be used to implement or practice the presently-disclosed subject matter, including but not limited to, diskettes, drives, and other magnetic-based storage media, optical storage media, including disks (e.g., CD-ROMS, DVD-ROMS, variants thereof, etc.), flash, RAM, ROM, and other memory devices, and the like.

The subject matter of embodiments of the present invention is described here with specificity, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications may be made without departing from the scope of the claims below.

What is claimed is:

1. A cryo-stimulation treatment device, comprising:
a needle having a proximal end and a distal end and a length therebetween, the needle configured to produce a cold zone for focused cold therapy, the needle having a cooling center along the length of the needle that is associated with a center of the cold zone produced by the needle;
an electrically insulated coating disposed about the length of the needle, wherein the needle is electrically conductive and wherein the proximal end of the needle is configured to couple with an electrical nerve stimulation generator that generates an electrical field about the distal end of the needle for electrically stimulating and locating a target nerve;
wherein the cooling center of the needle is uninsulated such that an intensity of the electrical field is coincident with the center of the cold zone produced by the needle; and
a handle defined by a housing,
wherein the needle is part of a replaceable needle assembly configured for releasable attachment to the handle, wherein the needle assembly incorporates an electrical port that electrically couples with an uninsulated portion of the proximal end of the needle, the electrical port configured to receive an input associated with the electrical nerve stimulation generator to releasably electrically couple the electrical nerve stimulation generator and the needle.

2. The treatment device of claim 1, wherein the electrically insulated coating comprises a fluoropolymer coating.

3. The treatment device of claim 1, wherein the electrically insulated coating comprises a silicone rubber coating.

4. The treatment device of claim 1, wherein the electrically insulated coating comprises a polyimide coating.

5. The treatment device of claim 1, wherein the electrically insulated coating comprises a parylene coating.

6. The treatment device of claim 1, wherein the electrically insulated coating comprises an epoxy coating.

7. The treatment device of claim 1, wherein the electrically insulated coating comprises a ceramic coating.

8. The treatment device of claim 1, wherein the needle is a first needle of a needle assembly having the first needle and a second needle adjacent the first needle, and wherein the second needle acts as an electrical ground during electrical stimulation of the nerve by the first needle.

9. A cryo-stimulation treatment device, comprising:
a needle assembly having:
one or more treatment needles configured to produce a cold zone for focused cold therapy of a target nerve;
one or more stimulation needles constructed of electrically conductive material and being configured to couple with an electrical nerve stimulation generator to produce an electrical field for stimulating the target nerve;
an electrically insulating coating on the one or more stimulation needles, wherein the one or more stimulation needles are uninsulated at a location of the one or more stimulation needles that is coincident with a center of the cold zone produced by the one or more treatment needles; and
a handle defined by a housing,
wherein the needle assembly is part of a replaceable needle assembly configured for releasable attachment to the handle, wherein the needle assembly incorporates an electrical port that electrically couples with the uninsulated portion of the one or more stimulation needles, the electrical port configured to receive an input associated with the electrical nerve stimulation generator to releasably electrically couple the electrical nerve stimulation generator and the one or more stimulation needles.

10. The treatment device of claim 9, wherein the one or more stimulation needles comprises a center needle and wherein the one or more treatment needles comprises at least two needles that are adjacent the center needle and on opposite sides of the center needle.

11. The treatment device of claim 9, wherein the one or more treatment needles comprises an electrically insulating coating and wherein at least a distal portion of the one or more treatment needles is uninsulated and acts as an electrical ground during electrical stimulation of the target nerve by the one or more stimulation needles.

12. The treatment device of claim 9, wherein the one or more treatment needles are also stimulation needles constructed of electrically conductive material and being configured to couple with the electrical nerve stimulation generator to produce an electrical field for stimulating the target nerve.

13. The treatment device of claim 9, wherein the electrically insulated coating comprises a fluoropolymer coating.

14. The treatment device of claim 9, wherein the electrically insulated coating comprises a silicone rubber coating.

15. The treatment device of claim 9, wherein the electrically insulated coating comprises a polyimide coating.

16. The treatment device of claim 9, wherein the electrically insulated coating comprises a parylene coating.

17. The treatment device of claim 9, wherein the electrically insulated coating comprises an epoxy coating.

18. The treatment device of claim 9, wherein the electrically insulated coating comprises a ceramic coating.

* * * * *